(12) United States Patent
Stuhlmann et al.

(10) Patent No.: US 9,820,923 B2
(45) Date of Patent: Nov. 21, 2017

(54) SUCCINATE DERIVATIVES

(71) Applicant: Symrise AG, Holzminden (DE)

(72) Inventors: Dominik Stuhlmann, Düsseldorf (DE); Imke Meyer, Bodenwerder (DE); Oskar Koch, Göttingen (DE); Helko Oertling, Lausanne (CH); Martina Herrmann, Hameln (DE); Claudia Gömann, Warbsen (DE)

(73) Assignee: Symrise AG, Holzminden (DE)

( * ) Notice: Subject to any disclaimer, the term of this patent is extended or adjusted under 35 U.S.C. 154(b) by 162 days.

(21) Appl. No.: 14/896,824

(22) PCT Filed: Jun. 4, 2014

(86) PCT No.: PCT/EP2014/061561
§ 371 (c)(1),
(2) Date: Dec. 8, 2015

(87) PCT Pub. No.: WO2014/198602
PCT Pub. Date: Dec. 18, 2014

(65) Prior Publication Data
US 2016/0128923 A1    May 12, 2016

(30) Foreign Application Priority Data
Jun. 9, 2013  (EP) .................................. 13171161

(51) Int. Cl.
| | | |
|---|---|---|
| A61K 8/00 | (2006.01) | |
| A61K 8/42 | (2006.01) | |
| A61Q 19/00 | (2006.01) | |
| A61Q 19/02 | (2006.01) | |
| A61Q 19/08 | (2006.01) | |
| C07C 235/74 | (2006.01) | |
| A61K 8/49 | (2006.01) | |
| A61Q 15/00 | (2006.01) | |
| A61Q 17/04 | (2006.01) | |
| A61Q 19/04 | (2006.01) | |

(52) U.S. Cl.
CPC .............. *A61K 8/42* (2013.01); *A61K 8/4926* (2013.01); *A61Q 15/00* (2013.01); *A61Q 17/04* (2013.01); *A61Q 19/00* (2013.01); *A61Q 19/007* (2013.01); *A61Q 19/02* (2013.01); *A61Q 19/04* (2013.01); *A61Q 19/08* (2013.01); *C07C 235/74* (2013.01); *A61K 2800/48* (2013.01); *A61K 2800/522* (2013.01); *A61K 2800/524* (2013.01); *A61K 2800/591* (2013.01)

(58) Field of Classification Search
CPC ........ A61K 2800/244; A61K 2800/412; A61K 8/25; A61K 8/88; A61K 8/0241; A61K 8/025; A61K 8/0254; A61K 8/046; A61Q 1/12; A61Q 5/004; A61Q 5/02; A61Q 5/06; A61Q 5/12
See application file for complete search history.

(56) References Cited

FOREIGN PATENT DOCUMENTS

| EP | 1 493 336 A2 | 1/2005 |
|---|---|---|
| WO | 2010/112710 A2 | 10/2010 |

*Primary Examiner* — Nannette Holloman
(74) *Attorney, Agent, or Firm* — Dilworth & Barrese, LLP

(57) ABSTRACT

The invention relates generally to new compounds of formula (I), wherein $R_1$, $R'_1$, $R_2$, $R'_2$, $R_3$, $R'_3$, $R_4$, $R'_4$, $R_5$, $R'_5$, $R_6$, $R_7$ are independently of one another and denote hydrogen, hydroxyl, $C_1$ to $C_6$-alkyl group or $R_6$ and $R_7$ form together a C5-C6 ring system, and wherein n=0, 1, 2, 3, or 4. Moreover, the invention relates to the use of one or more compounds of formula (I) in cosmetic or pharmaceutical compositions, which are preferably dermatological compositions and are preferably used topically.

(I)

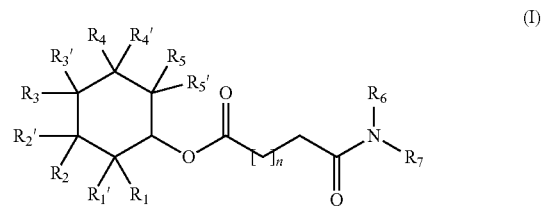

9 Claims, No Drawings

SUCCINATE DERIVATIVES

FIELD OF INVENTION

The invention relates generally to new succinate derivatives. Moreover, the invention relates to the use of one or more succinate derivatives in cosmetic or pharmaceutical compositions, which are preferably dermatological compositions and are preferably used topically.

STATE OF THE ART

Cellular ageing can be subdivided into two different processes. One is intrinsic ageing, caused by factors derived from inside the cells. The second is extrinsic ageing, caused by factors from the cells environment. The process of ageing leads to a plethora of cellular, metabolic and tissue-derived changes. Among these are—a decline in metabolic activity, a lower rate of cell division, a reduced DNA repair capacity, an accumulation of oxidized biomolecules (DNA, proteins, carbohydrates and lipids), an accumulation of misfolded proteins, cellular stiffening of vessel walls and an impaired peripheral blood circulation. All these aspects are closely interlinked with each other.

In premature skin aging one can observe changes within all the dermal layers: In the upper skin layer, the epidermis, one can usually observe a influence on the epidermal thickness. The epidermis becomes thinner with aging. This is caused by a reduced mitotic activity of keratinocytes within the stratum basale; the consequence is a reduced water-binding capacity, a lowered elasticity, a compromised barrier function and wrinkle formation. In the dermis, the amount of fibroblast decreases and their activity falls. The consequence is a reduced production of tropocollagen, hyaluronic acid and elastin that leads to a loss of elasticity, reduced sebum production and reduced perspiration. Among the most prominent processes within premature skin ageing is the chemical alteration of biomolecules. These modifications target intra- and extracellular proteins, nucleic acids or lipids and sugars. These alterations in turn, can result in diminished biological function. Examples are oxidation, carbonylation by ROS (reactive oxygen species), AGE-modifications (Advanced Glycation Endproducts) or lipidperoxidation.

UVB irradiation is a key factor during extrinsic skin aging and it alters cutaneous structure and function. Repeated exposure to UV radiation from the sun causes premature aging of skin. Under conditions of increased formation of oxidative stress as associated e.g. with UV irradiation, free radicals are formed, that cause damages to the cell contents and induced apoptosis, and aging. In particular, sunbathing and the visit of solarium amplify aging and support the formation of age spots, which result in additional premature skin ageing.

To combat wrinkles, which are visible signs of skin ageing, a lot of anti-ageing cosmetic products have been developed yet, which promote the reduction of wrinkles. Quite a series of facial products with various substances, e.g. vitamin C, vitamin E, Q10, lipoic acid, collagen and hyaluronic acid (HA) have been developed with the promise to be "wrinkles killer".

Proteasome Activity

Reactive oxygen species (ROS) are a major reason for skin aging. In lower concentrations these molecule are important signaling molecules. In elevated concentrations the effect becomes destructive ("oxidative stress"). The most prominent extrinsic ROS-inducer is the ultraviolet radiation. It leads to the formation of highly reactive hydroxyl radicals, superoxides, peroxides and other reactive species which can oxidize all kinds of biomolecules. Among these is the enzyme complex called proteasome. The proteasome functions as a proteolytic complex, degrading damaged or misfolded proteins. As the proteasome itself is a protein, the increased ROS-level lead to an accumulation of unwanted proteins, which cannot be degraded adequately anymore. This results in a vicious cycle where reactive oxygen damages the proteasome resulting in an impaired activity, resulting in more damaged proteasome. The proteasome degrades damaged, misfolded, oxidized or unnecessary proteins. It is involved in turn over regulation of proteins, cell cycle control, gene expression, (oxidative) stress, immune response and carcinogenesis. The proteasomal main function is the cell clearance of abnormal, denatured or in general damaged and unwanted proteins as well as for the regulated degradation of short-lived proteins. The efficacy of the degradation process is of enormous importance for the cellular homeostasis. The 20S proteasome is a cylindric structure, with a molecular weight of 700 kDa. It has a diameter of 12 nm and a length of 17 nm and consists of 4 rings, forming a tube like structure. The two outer rings are made of 7 different [alpha]-subunits. The other 2 rings build the middle structure of the 20S proteasome and consist of 7 diverse [beta]-subunits. The outer [alpha]-rings control the access of 20S-proteasome substrates into the inner proteolytic chamber. This proteolytic activity could be divided into three different parts: 1. Peptidyl-glutamyl-peptide-hydrolysing activity (caspase like activity); 2. Trypsin like activity and 3. Chymotrypsin like activity. The proteolytic action results in the generation of oligopeptides, generally with a length of 8-10 amino acids. In contrast to the 26S proteasome polyubiquitination is not necessary to degrade proteins. The 20S proteasome is ATP-independent.

In the skin the proteasome has an important role in ageing/photo-ageing. Following UV energy absorption there are different changes in the skin, including production of free radicals, modified proteins and 4-hydroxy-2-nonenal (HNE). These products affect the gene expression in skin cells and lead to an increase of matrix metalloproteinases (MMPs) and a decrease of their inhibitors (TIMPs) which results in a reduction of collagen and therefore in wrinkle formation. A drastic decline in proteasome activity and a simultaneous accumulation of modified and ubiquitinated proteins after UV irradiation in human keratinocytes has been reported. Today it is proven that there is a decline of proteasome activity and expression in human keratinocytes and fibroblasts during ageing. It is evident that this down regulation of proteasome activity is a result of protein aggregation. In a circuit, shrinking of proteasome activity leads to new protein aggregates and non degraded polyubiquitinated proteins, which in turn affect the proteasome again. Based on these findings, skin ageing is linked to proteasome dysfunction and preservation of "normal" proteasome function allays skin ageing. SDS and some fatty acids have been reported to stimulate proteasome activities in the test tube by favoring the open confirmation of the proteasome. Recently, isolated oleuropein, the most abundant of the phenolic compounds in *Olea europaea* leaf extract, olive oil and olives was shown to have stimulatory impact on proteasome activities. Furthermore, a *phaeodactylum* algae extract was reported to stimulate proteasome activity (WO 02/080876) as well as Palmitoyl Isoleucin. Besides the stimulation of proteasome activity by stimulation of one or more of the enzymatic activities, the upregulation of the proteasomal proteins itself is a potent method to induce the proteasomal degradation. This is of special interest regarding the fact that not only proteasomal activity declines in elderly people but also the expression of proteasomal subunits. Overexpression of proteasomal subunits in primary human embryonic fibroblasts and the accompanied increased rate of lipolysis were shown to extend the lifespan of these cells by 15-20%. Moreover, it was shown that restoration of the normal level of proteasome subunits in aged human fibroblasts reduces the level of ageing biomarkers. A decline of proteasome activities has been revealed in human primary cultures undergoing replicative senescence, whereas proteasome inhibition in young cells induces premature senescence.

Maintenance of cellular homeostasis influences the rate of ageing and is determined by several factors, including efficient proteolysis of damaged proteins. Protein degradation is predominantly catalyzed by the proteasome. Specifically, the proteasome is responsible for cell clearance of abnormal, denatured or in general damaged proteins as well as for the regulated degradation of short-lived proteins. As the proteasome has an impaired function during ageing, actives that restore its function are needed. Furthermore, UV irradiation impairs proteasomal function, thereby enhancing the cellular deposition of toxic proteins. Importantly, centenarians show a very high activity of the proteasome and are a good example of healthy ageing.

The activation of the proteasome is also linked to age-associated diseases, especially the neurodegenerative diseases in which misfolded proteins aggregate. Proteasome activators enhance the survival of Huntington's disease neuronal model cells and the development of Alzheimer's disease and Parkinson's disease is partly based on an inefficient proteasomal clearance.

Antioxidation

The most important intrinsic ROS source is the mitochondrion. This is a cellular organelle with the function to generate ATP, the driving force for nearly every biological function in the cellular metabolism. The mitochondrial electron transport chain does not work with 100% efficiency, thus generating misdirected electrons. These electrons finally lead to the generation of superoxides and therewith oxidative stress.

The strongest intracellular radical scavenging mechanism is the glutathione system. It combines enzymes like catalase and superoxide dismutase (SOD) that can dissipate free radicals. Even small doses of UV or other ROS generating circumstances can override these protective systems. Here, the addition of extrinsic antioxidants becomes important. Among these, there are two main possibilities to supply antioxidant power to a cell. One is the supply with chemical antioxidants. Molecules, those are capable of detoxifying ROS. A second strategy is to supply substances, which are able to induce intrinsic cellular antioxidative systems like Hemoxidase 1 (HO1).

Whitening

The loss of even skin tone due to an irregular distribution of collagen, haemoglobin and the formation of age spots are one of the most disturbing signs of ageing. Probably accumulated melanin and lipofuscin are responsible for the age spots, which is not clear yet. These age spots appear as invaginations of the basal membrane and a striking increase in the number of dermal papillae combined with irregular arranged melanin clusters was observed. Described for inflammatory response, the formation of age spots goes along with the upregulation of genes. The topical application of substances that bleach melanin, is the oldest approach to lighten age spots. Tyrosinase which is essential for the synthesis of new melanin, can be inhibit to lighten age spots. Reducing the amount of melanin produced, the prevention of melanocyte proliferation can be a useful strategy. In one form or another in melanin metabolism or catabolism Skin-lightening active ingredients intervene. Mostly brown to black melanind pigments are formed in the melanocytes of the skin. Then they are transferred to the keratinocytes and give the skin or hair its colour. Hydroxy-substituted aromatic amino acids such as L-tyrosine and L-DOPA, the yellow to red pheomelanins additionally from sulfur-containing molecules forms the brown-black eumelanins in mammals. For various reasons, skin-lightening agents are used: if for some reason the melanin-forming melanocytes in human skin are not evenly distributed, pigment spots occur which are either lighter or darker than the surrounding skin area. To balance out this pigment spots, skin lightening agents are sold which at least partially help. Aside from many people want to lighten their skin colour or to prevent skin pigmentation—so therefore the need is big of safe effective skin and hair lightening agents.

The therapeutic treatment of melanin-induced pigmentation disorders such as hyperpigmentations is one area of application (e.g. scar hyperpigmentations, post-traumatic drug-induced hyperpigmentations, post-inflammatory hyperpigmentations induced by phototoxic reactions, ephelides). Increasing in Skin pigmentation, caused by UV Light, can be avoided by using UV-absorbing substances. Merely inhibit the increase in skin pigmentation caused by UV light, the UV absorbers do not bring about a true lightening.

Therefore, object of the present invention was to provide compositions comprising active compounds, which have positive benefits to human skin cell, and thereby provide moisturizing and/or anti-ageing effects. In particular, the object was to provide active compounds which are capable to promote cell repair and regeneration, and thus prolong the health of cell life span of a cell in nucleus and cytoplasm in eukaryotes. The active compounds to be specified should be toxicologically safe, effective already at relatively low concentrations, well tolerated by the skin, stable (in particular in normal cosmetic and/or pharmaceutical formulations), and easy to formulate and economical to produce.

DESCRIPTION OF THE INVENTION

The subject of the invention relates to a compound of formula (I):

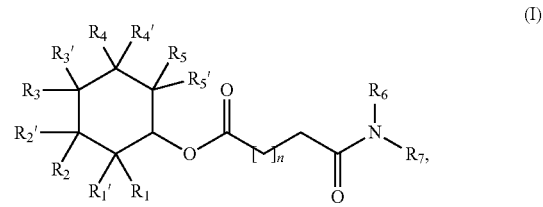

wherein $R_1$, $R'_1$, $R_2$, $R'_2$, $R_3$, $R'_3$, $R_4$ $R'_4$, $R_5$, $R'_5$, $R_6$, $R_7$ are independently of one another and denote hydrogen, hydroxyl, $C_1$ to $C_6$-alkyl group or $R_6$ and $R_7$ form together a C5-C6 ring system, and
wherein n=0, 1, 2, 3, or 4.

The term "or $C_1$ to $C_6$-alkyl group" represents alkyl moieties, which maybe branched or linear, and which maybe saturated or unsaturated. Preferred alkyl moieties maybe selected from the group consisting of methyl, ethyl, n-propyl, iso-propyl, n-butyl, iso-butyl, tert.-butyl, n-pentyl, 2-methylbutyl, neopentyl, hexyl, methylpentyl, dimethylbutyl, especially preferred are methyl, ethyl and iso-propyl.

The term "$R_6$ and $R_7$ form together a C5-C6 ring system" means that $R_6$ and $R_7$ and the nitrogen atom may form together a saturated or unsaturated ring, which are preferably not further substituted, preferred is that $R_6$ and $R_7$ and the nitrogen atom together form a six ring system, that is preferably a saturated hexyl ring system.

In a preferred embodiment of the invention $R_1$, $R'_1$, $R_2$, $R'_2$, $R_3$, $R'_3$, $R_4$, $R'_4$, $R_5$, $R'_5$ of formula (I) are independently of one another and denote hydrogen, methyl or isopropyl and n=0, 1 or 2.

In a further preferred embodiment $R_6$, $R_7$ of formula (I) are independently of one another and denote hydrogen, methyl, ethyl, isopropyl or $R_6$ and $R_7$ form together with the nitrogen of formula (I) a C6-ring system, which is preferably a saturated hexyl ring system.

In another preferred embodiment of the invention $R_1$, $R'_1$, $R_2$, $R'_2$, $R_3$, $R'_3$, $R_4$, $R'_4$, $R_5$, $R'_5$ of formula (I) are independently of one another and denote hydrogen, methyl or iso-propyl and n=0, 1 or 2 and $R_6$, $R_7$ are independently of one another and denote hydrogen, methyl, ethyl, isopropyl or $R_6$ and $R_7$ form together with the nitrogen of formula (I) a C6-ring system, which is preferably a saturated hexyl ring system.

In a preferred embodiment of the invention the compound of formula (I) is simplified to formula (II), in the case that $R'_1$, $R'_3$ and $R'_5$ denote hydrogen:

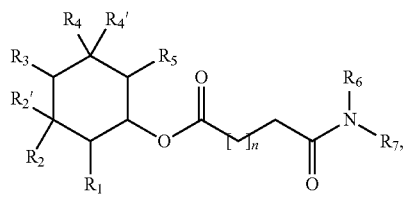

wherein $R_1$, $R_2$, $R'_2$, $R_3$, $R_4$ $R'_4$, $R_5$, $R_6$, $R_7$ are independently of one another and denote hydrogen, hydroxyl, $C_1$ to $C_6$-alkyl group or $R_6$ and $R_7$ form together a C5-C6 ring system, and
wherein n=0, 1, 2, 3, or 4.

In a preferred embodiment of the invention $R_1$, $R_2$, $R'_2$, $R_3$, $R_4$, $R'_4$, $R_5$ of formula (II) are independently of one another and denote hydrogen, methyl, or isopropyl and n=0, 1 or 2.

In a further preferred embodiment $R_6$, $R_7$ of formula (II) are independently of one another and denote hydrogen, methyl, ethyl, isopropyl or $R_6$ and $R_7$ form together with the nitrogen of formula (II) a C6-ring system, which is preferably a saturated hexyl ring system.

In another preferred embodiment of the invention $R_1$, $R_2$, $R'_2$, $R_3$, $R_4$, $R'_4$, $R_5$ of formula (II) are independently of one another and denote hydrogen, methyl or isopropyl and n=0, 1 or 2 and $R_6$, $R_7$ are independently of one another and denote hydrogen, methyl, ethyl, isopropyl or $R_6$ and $R_7$ form together with the nitrogen of formula (II) a C6-ring system, which is preferably a saturated hexyl ring system.

In another preferred embodiment the compounds of formula (I) and (II) are selected from the group of following compounds:
a) (1R,2S,5R)-2-isopropyl-5-methyl-cyclohexyl]4-(diisopropylamino)-4-oxo-butanoate (S1):

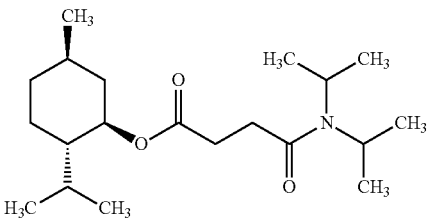

b) N,N-diethyl succinic acid amid-3,3,5-trimethylcyclohexylester (S2):

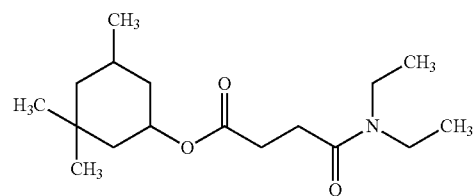

In which all enantiomeric and diasteriomeric forms are included, such as:
(1S,5R)-3,3,5-trimethylcyclohexyl)4-(diethylamino)-4-oxo-butanoate
(1R,5S)-3,3,5-trimethylcyclohexyl)4-(diethylamino)-4-oxo-butanoate
(1R,5R)-3,3,5-trimethylcyclohexyl)4-(diethylamino)-4-oxo-butanoate
(1S,5S)-3,3,5-trimethylcyclohexyl)4-(diethylamino)-4-oxo-butanoate
c) N,N-dimethyl succinic acid amid-2,3,6-trimethylcyclohexylester (S3):

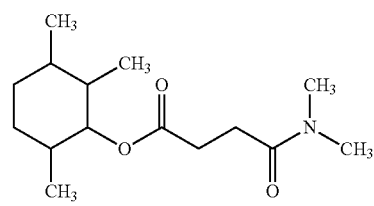

In which all enantiomeric and diasteriomeric forms are included, such as:
(1S,2S,5R)-(2,3,6-trimethylcyclohexyl)4-(dimethylamino)-4-oxo-butanoate
(1R,2S,5S)-(2,3,6-trimethylcyclohexyl)4-(dimethylamino)-4-oxo-butanoate
(1R,2S,5R)-(2,3,6-trimethylcyclohexyl)4-(dimethylamino)-4-oxo-butanoate
(1S,2R,5S)-(2,3,6-trimethylcyclohexyl)4-(dimethylamino)-4-oxo-butanoate
(1S,2R,5R)-(2,3,6-trimethylcyclohexyl)4-(dimethylamino)-4-oxo-butanoate
(1R,2R,5S)-(2,3,6-trimethylcyclohexyl)4-(dimethylamino)-4-oxo-butanoate
(1R,2R,5R)-(2,3,6-trimethylcyclohexyl)4-(dimethylamino)-4-oxo-butanoate
(1S,2R,5S)-(2,3,6-trimethylcyclohexyl)4-(dimethylamino)-4-oxo-butanoate d) 3,3,5-trimethylcyclohexyl-N-ethylsuccimat (S4):

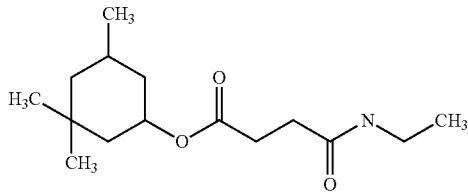
(V)

In which all enantiomeric and diasteriomeric forms are included, such as:

(1S,5R)-3,3,5-trimethylcyclohexyl]4-(ethylamino)-4-oxo-butanoate (1R,5S)-3,3,5-trimethylcyclohexyl]4-(ethylamino)-4-oxo-butanoate (1R,5R)-3,3,5-trimethylcyclohexyl]4-(ethylamino)-4-oxo-butanoate (1S,5S)-3,3,5-trimethylcyclohexyl]4-(ethylamino)-4-oxo-butanoate e) 2-(isopropylcyclohexyl)4-(dimethylamino)-4-oxo-butanoate (S5):

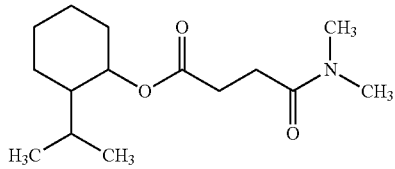
(VI)

In which all enantiomeric and diasteriomeric forms are included, such as:

(1S,2R)-2-(isopropylcyclohexyl)4-(dimethylamino)-4-oxo-butanoate (1R,2S)-2-(isopropylcyclohexyl)4-(dimethylamino)-4-oxo-butanoate (1R,2R)-2-(isopropylcyclohexyl)4-(dimethylamino)-4-oxo-butanoate (1S,2S)-2-(isopropylcyclohexyl)4-(dimethylamino)-4-oxo-butanoate f) (1R,2S,5R)-2-isopropyl-5-methyl-cyclohexyl]4-amino-4-oxo-butanoate (S6):

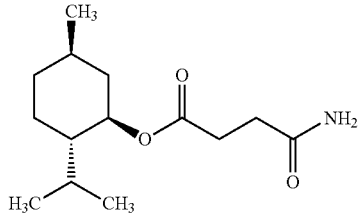
(VII)

g) N,N-Dimethyl-succinamic acid 3,3,5-trimethyl-cyclohexyl ester (S7):

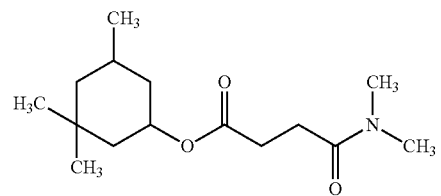
(VIII)

In which all enantiomeric and diasteriomeric forms are included, such as:

trans-3,3,5-trimethylcyclohexyl 4-(dimethylamino)-4-oxobutanoate (S7a) with:

(1S,5S)-3,3,5-trimethylcyclohexyl]4-(dimethylamino)-4-oxo-butanoate (S7a'):

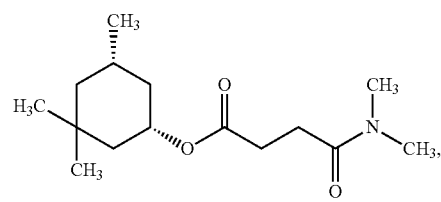
(VIIIa')

and (1R,5R)-3,3,5-trimethylcyclohexyl]4-(dimethylamino)-4-oxo-butanoate (S7a"):

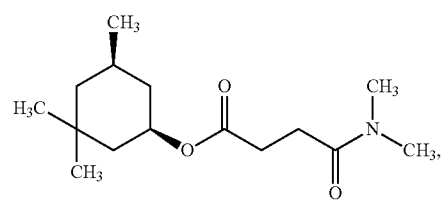
(VIIIa")

and cis-3,3,5-trimethylcyclohexyl 4-(dimethylamino)-4-oxobutanoate (S7b) with:

(1S,5R)-3,3,5-trimethylcyclohexyl]4-(dimethylamino)-4-oxo-butanoate (S7b')

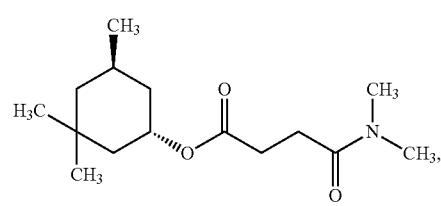
(VIIIb')

and (1R,5S)-3,3,5-trimethylcyclohexyl]4-(dimethylamino)-4-oxo-butanoate (S7b")

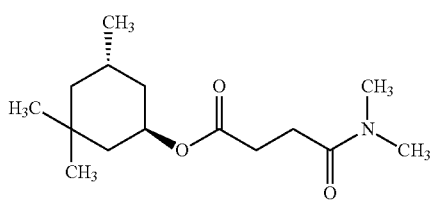

h) (3,3,5)-trimethylcyclohexyl)4-oxo-4-(1-piperidyl)butanoate (S8):

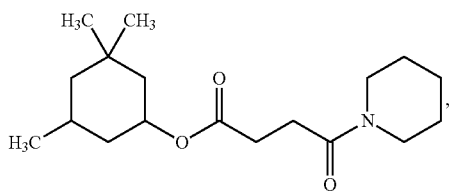

In which all enantiomeric and diasteriomeric forms are included, such as:
(1S,5R)-(3,3,5)-trimethylcyclohexyl)4-oxo-4-(1-piperidyl) butanoate
(1R,5S)-(3,3,5)-trimethylcyclohexyl)4-oxo-4-(1-piperidyl) butanoate
(1R,5R)-(3,3,5)-trimethylcyclohexyl)4-oxo-4-(1-piperidyl) butanoate
(1S,5S)-(3,3,5)-trimethylcyclohexyl)4-oxo-4-(1-piperidyl) butanoate i) 3,3,5-trimethylcyclohexyl)3-(dimethylamino)-3-oxo-propanoate (S9):

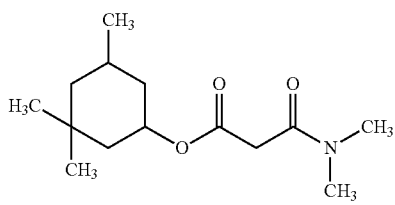

In which all enantiomeric and diasteriomeric forms are included, such as:
(1S,5R)-3,3,5-trimethylcyclohexyl)3-(dimethylamino)-3-oxo-propanoate
(1R,5S)-3,3,5-trimethylcyclohexyl)3-(dimethylamino)-3-oxo-propanoate
(1R,5R)-3,3,5-trimethylcyclohexyl)3-(dimethylamino)-3-oxo-propanoate
(1S,5S)-3,3,5-trimethylcyclohexyl)3-(dimethylamino)-3-oxo-propanoate j) 3,3,5-trimethylcyclohexyl)5-(dimethylamino)-5-oxo-pentanoate (S10):

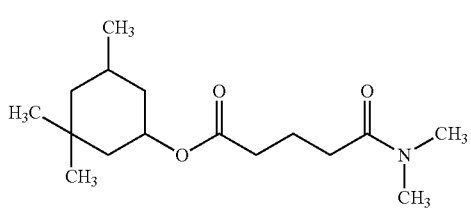

In which all enantiomeric and diasteriomeric forms are included, such as:
(1S,5R)-3,3,5-trimethylcyclohexyl)5-(dimethylamino)-5-oxo-pentanoate
(1R,5S)-3,3,5-trimethylcyclohexyl)5-(dimethylamino)-5-oxo-pentanoate
(1R,5R)-3,3,5-trimethylcyclohexyl)5-(dimethylamino)-5-oxo-pentanoate
(1S,5S)-3,3,5-trimethylcyclohexyl)5-(dimethylamino)-5-oxo-pentanoate.

Surprisingly, it was found that compounds of formula (I), respectively formula (II) have the ability to prolong health span of a cell. Especially, cellular repair mechanism in human skin can be activated, antioxidative effects can be observed and apoptosis can be reduced. It has been proved to be particularly advantageous to use a mixture of two compounds of formula (I), e.g. preferred are herewith a combination of trans-3,3,5-trimethylcyclohexyl 4-(dimethylamino)-4-oxobutanoate (S7a) and cis-3,3,5-trimethylcyclohexyl 4-(dimethylamino)-4-oxobutanoate (S7b). In case of enantiomeric mixtures such as described above every ratio between trans and cis isomer for the compounds of formula (I), respectively formula (II) is possible. Especially, preferred is a ratio of trans:cis from 1:200 to 200:1. Also preferred is the ratio from trans:cis from 1:60 to 50:1, more preferably 1:50 to 1:5, most preferably, 1:13 to 1:4. But the effects are also clearly positive when one of the enantiomeric forms is used alone.

Therefore, a preferred embodiment is N,N-Dimethyl-succinamic acid 3,3,5-trimethyl-cyclohexyl ester (S7), which is selected from the enantomeric form of
trans-3,3,5-trimethylcyclohexyl 4-(dimethylamino)-4-oxobutanoate (S7a) with:
(1S,5S)-3,3,5-trimethylcyclohexyl]4-(dimethylamino)-4-oxo-butanoate (S7a') and/or
(1R,5R)-3,3,5-trimethylcyclohexyl]4-(dimethylamino)-4-oxo-butanoate (S7a").

Another preferred embodiment is N,N-Dimethyl-succinamic acid 3,3,5-trimethyl-cyclohexyl ester (S7), which is selected from the enantomeric form of
cis-3,3,5-trimethylcyclohexyl 4-(dimethylamino)-4-oxobutanoate (S7b) with:
(1S,5R)-3,3,5-trimethylcyclohexyl]4-(dimethylamino)-4-oxo-butanoate (S7b') and/or
(1R,5S)-3,3,5-trimethylcyclohexyl]4-(dimethylamino)-4-oxo-butanoate (S7b").

Also preferred is a mixture of (1R,2S,5R)-2-isopropyl-5-methyl-cyclohexyl]4-(diisopropylamino)-4-oxo-butanoate (S1) and N,N-diethyl succinic acid amid-3,3,5-trimethylcyclohexylester (S2).

Also preferred is a mixture of N,N-dimethyl succinic acid amid-2,3,6-trimethylcyclohexylester (S3) and 2-(isopropyl-cyclohexyl)4-(dimethylamino)-4-oxo-butanoate (S5).

Also preferred is an enantiomeric mixture of 3,3,5-trimethylcyclohexyl)3-(dimethylamino)-3-oxo-propanoate (S9), comprises of
(1S,5R)-3,3,5-trimethylcyclohexyl)3-(dimethylamino)-3-oxo-propanoate and/or
(1R,5S)-3,3,5-trimethylcyclohexyl)3-(dimethylamino)-3-oxo-propanoate and/or
(1R,5R)-3,3,5-trimethylcyclohexyl)3-(dimethylamino)-3-oxo-propanoate and/or
(1S,5S)-3,3,5-trimethylcyclohexyl)3-(dimethylamino)-3-oxo-propanoate.

In case of enantiomeric mixtures such as described above every ratio between trans and cis isomers for the compounds of formula (I), respectively formula (II) is possible. Especially preferred is a ratio of trans:cis from 1:200 to 200:1. Also preferred is the ratio from trans:cis is from 1:60 to 50:1, more preferably 1:50 to 1:5, most preferably, 1:13 to 1:4.

But in particular it has been proved that the compounds of formula (I), respectively formula (II), especially the compounds S1, S2, S3, S4, S5, S6, S7, S8, S9 and S10 are alone, also in their enantiomeric form are active and benefits to the skin as described above.

In particular, the enantiomeric forms alone, e.g. S7a' or S7a" or S7b' or S7b" are advantageous, for that the single enantiomeric forms already have the ability to prolong health span of a cell, especially, cellular repair mechanism in human skin can be activated, antioxidative effects can be observed and apoptosis can be reduced.

Therefore, an object of the invention is one or more compounds of formula (I), respectively formula (II) for use in the treatment of cellular ageing and cell life span.

And a further object of the invention is one or more compounds of formula (I), respectively formula (II) for use in the treatment of free-radical activity, in the form that the renewal and differentiation of keratinocytes is regulated, the functional condition of the skin is improved of is kept in good functional condition, for skin protection or treating dry skin.

A concentration of from about 0.001 to 15%, preferred 0.1 to 2%, and most preferred 0.01 to 5.0% by weight of the compound of formula (I), respectively formula (II) in a pharmaceutical or cosmetic composition is preferred, in case of more than two compounds of formula (I), respectively formula (II), the sum of all compounds of formula (I), respectively formula (II) is meant.

It was also found that one or more compounds of formula (I), respectively formula (II) can be used for activation and/or reactivation and/or protection of proteasome in nucleus and cytoplasm in eukaryotes.

The term "one or more compounds of formula (I), respectively formula (II)" means that a mixture of two or more kind of compound of formula (I), respectively formula (II) maybe also possible used.

As proteasome has an impaired function as already described above, during aging it is important to protect, activate or reactivate proteasome, thus positively contributing to affect the anti-ageing.

A further object of the invention is the use, especially the cosmetically use of one or more compounds of formula (I), respectively formula (II) is especially for the treatment of cellular ageing and prolongation of cell life span, which is preferably in the form of anti-aging, delaying aging, toning, moisturizing and/or whitening. In particular, in a preferred embodiment the one or more compounds of formula (I) is used for activation and/or reactivation and/or protection of proteasome in nucleus and cytoplasm in eukaryotes.

In another preferred embodiment the one or more compounds of formula (I), respectively formula (II) are used as active substances in the preparation of a cosmetical or pharmaceutical composition, which are preferably dermatological compositions, preferably for topical use on the skin.

The term "active substances" means that compounds according to formula (I), respectively formula (II) show in an effective amount effects and benefits to the skin that contributes to skin health care, e.g. ageing, antioxidative effects, depigmentation, whitening.

In particular, the one or more compounds of formula (I), respectively formula (II) have an anti-free-radical activity, thus when these active substances are formulated in cosmetic or pharmaceutical compositions, the compositions regulating the renewal and differentiation of the keratinocytes, for improving the functional condition of the skin or keeping them in a good functional condition, for skin protection or treating dry skin. Therefore, in another preferred embodiment the one or more used compounds of formula (I), respectively formula (II) have an anti-free-radical activity, thus regulating the renewal and differentiation of the keratinocytes, for improving the functional condition of the skin or keeping them in a good functional condition, for skin protection or treating dry skin.

In a preferred embodiment of the invention the one or more compounds of formula (I), respectively formula (II) is N,N-Dimethyl-succinamic acid 3,3,5-trimethyl-cyclohexyl ester (S7), wherein all enantiomeric and diastereomeic forms are incorporated herewith. Especially, in a preferred embodiment of the invention the used one or more compounds of formula (I), respectively formula (II) is trans-3,3,5-trimethylcyclohexyl 4-(dimethylamino)-4-oxobutanoate (s7a),
and/or
cis-3,3,5-trimethylcyclohexyl 4-(dimethylamino)-4-oxobutanoate (s7b),
wherein the ratio of trans:cis is about 1:200 to 200:1.

Industrial Application

More particularly, the present invention also refers to a non-therapeutic (rather cosmetic) method for activation and/or reactivation and/or protection of proteasome in nucleus and cytoplasmin eukaryotes, wherein one or more compounds of formula (I)

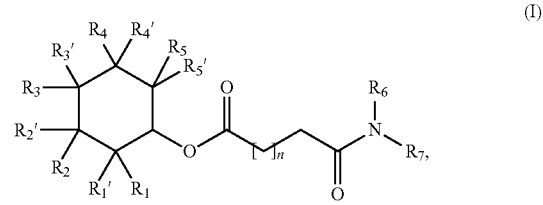

(I)

wherein $R_1$, $R'_1$, $R_2$, $R'_2$, $R_3$, $R'_3$, $R_4$ $R'_4$, $R_5$, $R'_5$, $R_6$, $R_7$ are independently of one another and denote hydrogen, hydroxyl, $C_1$ to $C_6$-alkyl group or $R_6$ and $R_7$ form together a C5-C6 ring system, and
wherein n=0, 1, 2, 3, or 4
is administered to human tissue or skin.

In a preferred embodiment of the invention the compound of formula (I) is simplified to formula (II), in the case that $R'_1$, $R'_3$ and $R'_5$ denote hydrogen thus formula (I) can be represent as follows:

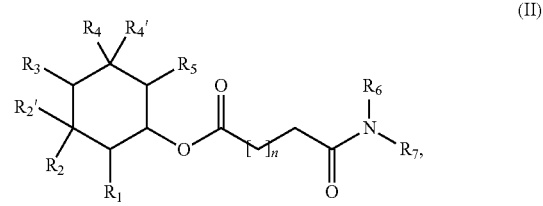

(II)

wherein $R_1$, $R_2$, $R'_2$, $R_3$, $R_4$ $R'_4$, $R_5$, $R_6$, $R_7$, are independently of one another and denote hydrogen, hydroxyl, $C_1$ to $C_6$-alkyl group or $R_6$ and $R_7$ form together a C5-C6 ring system, and
wherein n=0, 1, 2, 3, or 4.

In one embodiment the present invention refers to a method for affecting a skin care treatment, comprising topically applying to the skin a skin care efficient amount of one or more of a compound of formula (I), respectively formula (II). Skin care treatment is preferably, for whitening or for reducing signs of aging.

In another embodiment the present invention refers to a method for the treatment of the epidermis of human beings suffering from the signs of aging, suffering from dry skin and for the prevention of maladies associated with free radical formation on skin, comprising topically administering an effective amount of one or more compounds of formula (I), respectively formula (II) to the epidermis.

Pharmaceutical Compositions

The compounds of formula (I), respectively formula (II) can easily be incorporated in the given concentrations in common pharmaceutical compositions.

It is specifically contemplated that pharmaceutical compositions may be prepared using a pharmacological concentration of the active compounds or its salts disclosed in the present invention. It is not intended that the present invention be limited by the particular nature of the therapeutic preparation, so long as the preparation comprises the active agent or its salts. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts. A person having ordinary skill in this art would readily be able to deter-mine, without undue experimentation, the appropriate dosages and routes of administration of ascorbic acid of the present invention.

Thus, a further object of the invention is one or more compounds of formula (I), respectively formula (II) as a medicament.

In a preferred embodiment the one or more compounds of formula (I), respectively formula (II) is for use in the treatment of cellular ageing and cell life span, the treatment of free-radical activity, in the form that the renewal and differentiation of keratinocytes is regulated, the functional condition of the skin is improved of is kept in good functional condition, for skin protection or treating dry skin.

A preferred embodiment of the present invention relates to pharmaceutical compositions, comprising
(a) one or more of an active compound of formula (I)

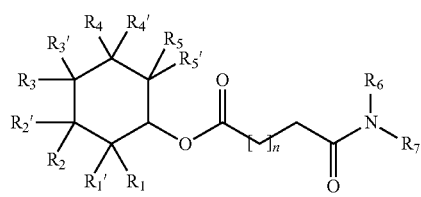

(I)

wherein $R_1$, $R'_1$, $R_2$, $R'_2$, $R_3$, $R'_3$, $R_4$ $R'_4$, $R_5$, $R'_5$, $R_6$, $R_7$ are independently of one another and denote hydrogen, hydroxyl, $C_1$ to $C_6$-alkyl group or $R_6$ and $R_7$ form together a C5-C6 ring system, and
wherein n=0, 1, 2, 3, or 4, and
(b) at least one pharmaceutical additive, and
(c) at least one pharmaceutically acceptable carrier.

In a preferred embodiment of the invention the compound of formula (I) is simplified to formula (II), in the case that $R'_1$, $R'_3$ and $R'_5$ denote hydrogen as have been already described above.

Cosmetic Compositions

The compounds of formula (I), respectively formula (II) can easily be incorporated in the given concentrations in common cosmetic compositions such as pump sprays, aerosol sprays, creams, ointments, tinctures, lotions and the like without having an odorous, colouring or sensating effect. In this case, it is also possible and in many cases advantageous to combine the compounds of formula (I), respectively formula (II) with further active ingredients.

Therefore another object of the invention is the cosmetical use of one or more compounds of formula (I), respectively formula (II) for the treatment of anti-aging, delaying aging, toning, moisturizing and/or whitening. Especially, the cosmetical use of one or more compounds of formula (I), respectively formula (II) is preferably for activation and/or reactivation and/or protection of proteasome in nucleus and cytoplasm in eukaryotes. Another preferred embodiment is the use of one or more compounds of formula (I), respectively formula (II), wherein the one or more compounds of formula (I) or (II) have an anti-free-radical activity, thus regulating the renewal and differentiation of the keratinocytes, for improving the functional condition of the skin or keeping them in a good functional condition, for skin protection or treating dry skin.

The compositions according to the present invention can be produced by conventional processes known per se, such that one or more compounds of formula (I), respectively formula (II) are incorporated into products particularly for topical application which can have a conventional composition and which in addition to the effects mentioned hereinbefore or hereinafter can also be used for the treatment, care and cleansing of the skin or hair.

A preferred embodiment of the present invention relates to cosmetic compositions, comprising
(a) one or more of an active compound of formula (I)

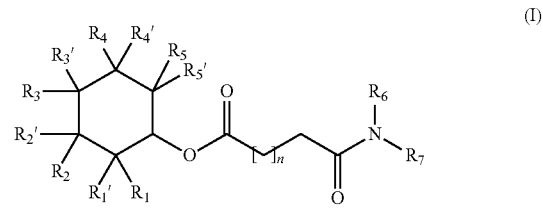

(I)

wherein $R_1$, $R'_1$, $R_2$, $R'_2$, $R_3$, $R'_3$, $R_4$ $R'_4$, $R_5$, $R'_5$, $R_6$, $R_7$ are independently of one another and denote hydrogen, hydroxyl, $C_1$ to $C_6$-alkyl group or $R_6$ and $R_7$ form together a C5-C6 ring system, and
wherein n=0, 1, 2, 3, or 4, and
(b) at least one cosmetic additive, and
(c) at least one cosmetically acceptable carrier.

In a preferred embodiment of the invention the compound of formula (I) is simplified to formula (II), in the case that $R'_1$, $R'_3$ and $R'_5$ denote hydrogen as have been already described above.

The cosmetic or pharmaceutical acceptable carriers are, preferably, selected from the group consisting of water, alcohols containing 2 to 6 carbon atoms, polyols containing 1 to 10 carbon atoms and 2 to 4 hydroxyl groups and oil bodies. Particularly preferably are, besides water, ethanol, isopropyl alcohol, ethylene glycol, propylene glycol, glycerol, trimethylolpropane, pentaerythritol and esters of linear or branched, saturated, and, particularly, unsaturated fatty acids containing 6 to 22, and, preferably, 8 to 18 carbon atoms with alcohols containing 1 to 6 carbon atoms.

The cosmetic or pharmaceutical compositions according to the invention may contain components (a) and (b) in the weight ratio of from 0.1:99 to 99.9:1, preferably, of from 10:90 to 90:10, more preferably of from 25:75 to 75:25, and most preferably of from 40:60 to 60:40. Components (a+b) and (c) may be contained in the weight ratio of from 0.01:99.9 to 2:98, preferably of from 0.5:99.5 to 1.5:98.5, and specifically of about 1:99.

The cosmetic or pharmaceutical compositions according to the invention preferably comprise as active substance of compound (I) and respectively formula (II):

trans-3,3,5-trimethylcyclohexyl 4-(dimethylamino)-4-oxobutanoate (s7a) and and/or cis-3,3,5-trimethylcyclohexyl 4-(dimethylamino)-4-oxobutanoate (s7b) in the ratio of trans:cis is about 1:200 to 1:6.

The trans-3,3,5-trimethylcyclohexyl 4-(dimethylamino)-4-oxobutanoate (s7a) may be preferably both Enantiomer (1S,5R)-3,3,5-trimethylcyclohexyl]4-(dimethylamino)-4-oxo-butanoate and/or (1R,5S)-3,3,5-trimethylcyclohexyl]4-(dimethylamino)-4-oxo-butanoate:

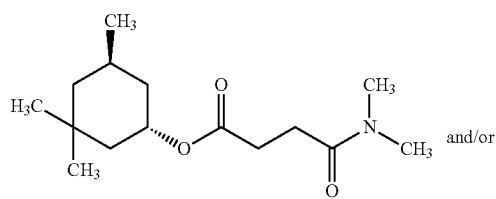

(VIIIb')

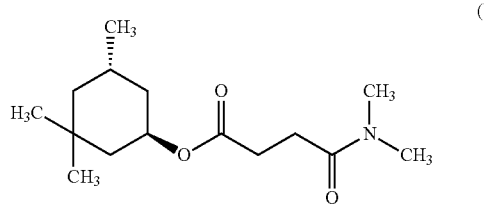

(VIIIb")

and the cis-3,3,5-trimethylcyclohexyl 4-(dimethylamino)-4-oxobutanoate (s7b) is may be preferably both Enantiomer (1R,5R)-3,3,5-trimethylcyclohexyl]4-(dimethylamino)-4-oxo-butanoate and/or (1S,5S)-3,3,5-trimethylcyclohexyl]4-(dimethylamino)-4-oxo-butanoate:

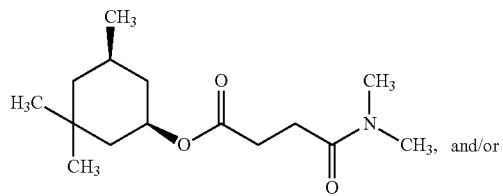

(VIIIa")

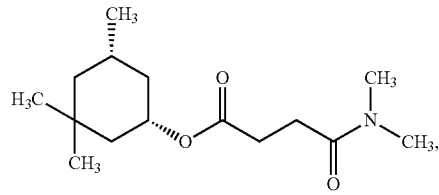

(VIIIa')

It has been shown that such a mixture of trans-3,3,5-trimethylcyclohexyl 4-(dimethylamino)-4-oxobutanoate and cis-3,3,5-trimethylcyclohexyl 4-(dimethylamino)-4-oxobutanoate has antioxidative properties, which benefits to skin healthcare. Further, the mixture shows a good activation and/or reactivation and/or protection effect for proteasom, which benefits to cell life span.

But a mixture of only single enantiomers in a pharmaceutical or cosmetic composition is also as active as a mixture of enantiomeric forms. Thus in a preferred embodiment the pharmaceutical or cosmetic composition comprises one or more compounds of formula (I), respectively formula (II), wherein the compounds of formula (I), respectively formula (II) is selected from the group of consisting of compounds S1, S2, S6, S7, S8, S9, S10 and wherein the compounds are selected individual, such that each enantiomeric form of S1, S2, S6, S7, S8, S9, S10 as described above can be selected solely. Preferred is a cosmetic or pharmaceutical composition which comprises one or more compounds of formula (I), respectively formula (II) selected from S7a' and/or 7a" and/or S7b' and/or S7b".

The cosmetic or pharmaceutical compositions according to the invention may comprises further additives which are selected from the group consisting of surfactants, oil bodies, emulsifiers, superfatting agents, pearlising waxes, consistency factors, polymers, silicone compounds, waxes, stabilizers, antidandruff agents, film formers, swelling agents, hydrotropes, preservatives, solubilizers, complexing agents, reducing agents, alkalising agents, perfume oils, dyes, thickeners, fats, lecithins, phospholipids, UV protection factors, moisturizers, biogenic agents, antioxidants, deodorants, antiperspirants, insect repellants, self-tanning agents, tyrosine inhibitors (depigmenting agents), and the like as additional auxiliaries and additives.

More particularly, the additives are selected from the group consisting of
(b1) antioxidants;
(b2) primary or secondary sun protection factors, in particular substances which absorb or reflect UV radiation, preferably UV-filters (UV-absorbers) for cosmetic purposes, in particular for skin-protecting purposes;
(b3) matrix-metalloproteinase (MMP) inhibitors;
(b4) moisturizing agents, preferably selected from the group consisting of alkane diols or alkane triols;
(b5) glycosaminoglycans (GAGs) and further substances stimulating the synthesis of glycosaminoglycans;
(b6) anti-inflammatory agents;
(b7) TRPV1 antagonists;

A cosmetic composition, preferably a topical preparation according to the invention containing
(a) one or more active compounds of formula (I), respectively formula (II) and
(b) one or more cosmetic additives selected from the above mentioned group of component (b1) to (b7)

allows to achieve an overall higher, i.e. more pronounced moisturizing and/or anti-ageing effect. Said more pronounced anti-ageing action is, at least partly, based on synergistic effects.

Anti-ageing Additives

In the context of the invention, anti-ageing or biogenic agents are, for example antioxidants, primary or second dary sun protection factors, matrix-metalloproteinase inhibitors (MMPI), skin moisturizing agents, glycosaminglycan stimulators, anti-inflammatory agents and TRPV1 antagonists.

(b1) Antioxidants. amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxin, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligo-glyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, *sophora, pueraria, pinus*, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

(b2) Primary and secondary sun protection factors. Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazole sulfonic acid and salts (Neo Heliopan®Hydro)
3-(4'-trimethylammonium)benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan®MBC)
3-benzylidene-D,L-camphor
N-[(2 and 4)-[2-(oxoborn-3-ylidene)methyl]benzyl] acrylamide polymer
4,4'-[(6-[4-(1,1-dimethyl)aminocarbonyl)phenylamino]-1,3,5-triazine-2,4-diyl)-diimino]-bis-(benzoic acid-2-ethylhexyl ester) (Uvasorb®HEB)
benzylidene malonate polysiloxane (Parsol®SLX)
glyceryl ethylhexanoate dimethoxycinnamate
dipropylene glycol salicylate
tris(2-ethylhexyl)-4,4',4"-(1,3,5-triazine-2,4,6-triyltriimino)tribenzoate (=2,4,6-trianilino-(p-carbo-2'-ethylhexyl-r-oxy)-1,3,5-triazine) (Uvinul®T150)

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3(1,3,3,3-tetramethyl-1-(trimethylsilyl)oxy)disiloxyanyl)propyl) (Mexoryl®XL)
2,2'-methylene bis-(6-(2H-benzotriazol-2-yl)-4-1,1,3,3-tetramethylbutyl)phenol) (Tinosorb®M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxy)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methylpropyloxy)-2-hydroxy}phenyl]-6-(4-methoxyphenyl)-1,3,5-triazine UV-A filters which are preferably combined with one or more compounds of formula (I) in a preparation according to the present invention are selected from the group consisting of
4-isopropyl dibenzoyl methane
terephthalylidene dibornane sulfonic acid and salts (Mexoryl®SX)
4-t-butyl-4'-methoxydibenzoyl methane (avobenzone)/ (Neo Heliopan®357)
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
2-(4-diethylamino-2-hydroxybenzoyl)benzoic acid hexyl ester (Uvinul®A Plus)
indanylidene compounds in accordance with DE 100 55 940 A1 (=WO 2002 038537 A1)

UV filters which are more preferably combined with one or more compounds of formula (I) in a preparation according to the present invention are selected from the group consisting of
p-aminobenzoic acid
3-(4'-trimethylammonium)benzylidene bornan-2-one methyl sulfate
salicylic acid homomenthyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene)methyl]benzyl] acrylamide polymer
p-methoxycinnamic acid-2-ethylhexyl ester (Neo Heliopan®AV)
p-aminobenzoic acid ethyl ester (25 mol) ethoxylated (INCI name: PEG-25 PABA)
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3(1,3,3,3-tetramethyl-1-(trimethylsilyl)oxy)disiloxyanyl) propyl) (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan®MBC)
3-benzylidene camphor salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine (Tinosorb®S)
benzylidene malonate polysiloxane (Parsol®SLX)
menthyl anthranilate (Neo Heliopan®MA)
2-(4-diethylamino-2-hydroxybenzoyl)benzoic acid hexyl ester (Uvinul® A Plus)
indanylidene compounds in accordance with DE 100 55 940 (=WO 20202 038537 A1).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and heptathionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

(b3) Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonyl-fluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and *lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 2002 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

(b4) Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

(b5) Glycosaminoglycan stimulators. Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl AminobutyroylvalylaminobutyricUrea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.

(b6) Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willowherb, oats, calendula, *arnica*, St John's wort, honeysuckle, rosemary, *Passiflora incarnata*, witch hazel, ginger or *Echinacea*; preferably selected from the group consisting of extracts or fractions from camomile, Aloe vera, oats, calendula, *arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-) ceramides [preferably Ceramide 2, hydroxypropyl bispalmitamide MEA, cetyloxy-propyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

(b7) TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

In case vitamin A and/or a derivative of vitamin A is used as component (b1) or as constituent of component (b1), the total amount thereof preferably is in the range of from 0.1 to 3% b.w., based on the total weight of the preparation.

In case vitamin E and/or a derivative of vitamin E is used as component (b1) or as constituent(s) of component (b1), the total amount thereof preferably is in the range of from 0.1 to 2% b.w., based on the total weight of the preparation.

In case vitamin C and/or a derivative of vitamin C is used as component (b1) or as constituent of component (b-1), the total amount thereof preferably is in the range of from 0.01 to 3% b.w., based on the total weight of the preparation.

In case ubiquinone is used as component (b1) or as constituent of component (b1), the total amount thereof preferably is in the range of from 0.001 to 0.1% b.w., based on the total weight of the preparation.

In case hyaluronic acid and/or a derivative or salt of hyaluronic acid is used as component (b5) or as constituent of component (b5), the total amount thereof preferably is in the range of from 0.01 to 3% b.w., based on the total weight of the preparation.

In case Retinol and/or a derivative of retinol is used as component (b5) or as constituent of component (b5), the total amount thereof preferably is in the range of from 0.01 to 1% b.w., based on the total weight of the preparation.

In case alpha-bisabolol (natural or synthetic) is used as component (b5) or as constituent of component (b5), the total amount thereof preferably is in the range of from 0.01 to 0.5% b.w., based on the total weight of the preparation.

In case oat glucan is used as component (b5) or as constituent of component (b5), the total amount thereof preferably is in the range of from 0.01 to 1% b.w., based on the total weight of the preparation.

In case *Echinacea purpurea* extract is used as component (b5) or as constituent of component (b5), the total amount thereof preferably is in the range of from 0.1 to 0.6% b.w., based on the total weight of the preparation.

In case *Alpinia galanga* leaf extract is used as component (b5) or as constituent of component (b5), the total amount thereof preferably is in the range of from 0.1 to 5% b.w., based on the total weight of the preparation.

In case *Sinorhizobium Meliloti* Ferment Filtrate is used as component (b5) or as constituent of component (b-5), the total amount thereof preferably is in the range of from 0.1 to 5% b.w., based on the total weight of the preparation.

In case Tetradecyl Aminobutyroylvalylaminobutyric Urea Trifluoroacetate is used as component (b5) or as constituent of component (b5), the total amount thereof preferably is in the range of from 0.1 to 3% b.w., based on the total weight of the preparation.

In case Retinyl palmitate is used as component (b3) or as constituent of component (b-3), the total amount thereof preferably is in the range of from 1 to 3% b.w., based on the total weight of the preparation.

In case Ursolic acid is used as component (b3) or as constituent of component (b-3), the total amount thereof preferably is in the range of from 0.01 to 1% b.w., based on the total weight of the preparation.

In case one or more than one extract from the leaves of the Rosaceae family, sub-family Rosoideae is used as component (b3) or as constituent of component (b-3), the total amount thereof preferably is in the range of from 0.01 to 3% b.w., based on the total weight of the preparation.

In case Genistein and/or Daidzein is used as component (b3) or as constituent of component (b3), the total amount thereof preferably is in the range of from 0.01 to 2% b.w., based on the total weight of the preparation.

Additional Additives

A cosmetic composition, preferably a topical preparation according to the invention containing
(a) one or more active compounds of formula (I) and
(b) one or more active ingredient selected from the above mentioned group of component (b)
have shown to exhibit particularly improved efficacy, in particular faster and/or stronger moisturizing and/or anti-ageing activity. In many cases a more than additive, often synergistic, activity was observed.

As mentioned above, proteasom, can be significantly degraded by free radicals. The combination of one or more compounds of formula (I), respectively formula (II) and one or more antioxidants of component (b1) is particularly beneficial because antioxidants additionally protect proteasom from reactive oxygen species.

The combination of one or more compounds of formula (I), respectively formula (II) and one or more sun protection factors of component (b2) is particularly beneficial because UV light is one major source for reactive oxygen species. Furthermore as mentioned above, collagen fragments in the dermis resulting from UVB-induced collagen degradation and strongly reduced proteasom in human skin. Particular advantageous are therefore cosmetic, dermatological and/or pharmaceutical preparations according to the invention which additionally include one or more UV filters (UV absorbers) and which thus act as compositions with proteasom stimulating activity and additionally as a sunscreen, overall resulting in a higher, improved proteasom level.

The combination of one or more compounds of formula (I), respectively formula (II) and one or more agents selected from the group consisting of matrix-metalloproteinase (MMP) inhibitor (b3) is particularly beneficial resulting in an overall higher, improved proteasom level.

The combination of one or more compounds of formula (I), respectively formula (II) and one or more skin moisturizing agents (b4) is particularly beneficial because skin moisturizing agents additionally improve the moisture status of the skin.

The combination of one or more compounds of formula (I) and one or more agents selected from the group consisting of glycosaminoglycans (GAGs) and further substances stimulating the synthesis of glycosaminoglycans (b5) is particularly beneficial resulting in an overall higher, improved GAG level.

It has been found rather advantageous to add the anti-ageing actives forming components (b1) to (b7) to the respective compositions in the following amounts:

the total quantity of antioxidants of component (b1) is in the range of from about 0.001 to about 10% b.w. preferably in the range of from about 0.01 to about 5% b.w., more preferably in the range of from about 0.05 to about 3% b.w. and/or the total quantity of sun protection factors (UV filters and/or absorbers) of component (b2) is in the range of from about 0.01 to about 40% b.w., preferably in the range of from about 0.1 to about 30% by weight, more preferably in the range of from about 0.2 to about 20% by weight, even more preferably in the range of from about 0.5 to about 15% by weight, in particular in the range of from about 1.0 to about 10% by weight, and/or the total quantity of matrix-metalloproteinase (MMP) inhibitors of component (b3) is in the range of from about 0.01 to about 5% b.w. preferably in the range of from about 0.01 to about 3% b.w. more preferably in the range of from about 0.05 to about 2% b.w. and/or the total quantity of skin moisturizing agents of component (b4) is in the range of from about 0.1 to about 30% b.w, preferably in the range of from about 0.25 to about 20% b.w. more preferably in the range of from about 0.5 to about 10% b.w., even more preferably in the range of from about 1 to about 5% b.w. and/or the total quantity of glycosaminoglycans and substances stimulating the synthesis of glycosaminoglycans of component (b5) is in the range of from about 0.01 to about 10% b.w. preferably in the range of from about 0.05 to about 5% b.w., more preferably in the range of from about 0.1 to about 3% b.w., the total quantity of anti-inflammatory agents of component (b6) is in the range of from about 0.01 to about 10% b.w. preferably in the range of from about 0.05 to about 5% b.w., more preferably in the range of from about 0.1 to about 3% b.w., the total quantity of TRVP1 antagonists of component (b5) is in the range of from about 0.001 to about 5% b.w. preferably in the range of from about 0.01 to about 3% b.w., more preferably in the range of from about 0.05 to about 2% b.w., in each case based on the total weight of the composition.

1. Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

2. Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

3. Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

(i) Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

(ii) Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

(iii) Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

(iv) Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

(v) Amphoteric emulsifiers. Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

4. Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

5. Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

6. Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl ace-tate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

7. Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

8. Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

9. Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and micro-waxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

10. Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (1-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy-)acetate, menthylpyroglutamate), menthylcarbonates (for example menthylpropylenegly-colcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

11. Anti-microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

12. Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

13. Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxy-allantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

14. Film Formers and Anti-dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethyl-pentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

15. Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

16. Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

17. Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, *angelica*, celery, cardamom, *costus*, iris, *calmus*), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*galbanum*, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, •-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, *galbanum* oil, *ladanum* oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

18. Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation. It should be noted that the information on additives and their ranges for cosmetic compositions are also valid for pharmaceutical or dermatalogical formulations.

Encapsulation

Although one preferred embodiment of the present invention relates to topical application, the compositions may also be administered orally, preferably in the form of a capsule. The compositions are typically encapsulated by means of a solid covering material, which is preferably selected from starches, degraded or chemically or physically modified starches (in particular dextrins and maltodextrins), gelatins, gum arabic, agar-agar, ghatti gum, gellan gum, modified and non-modified celluloses, pullulan, curdlan, carrageenans, alginic acid, alginates, pectin, inulin, xanthan gum and mixtures of two or more of said substances.

The solid covering material is preferably selected from gelatin (preferred are pork, beef, chicken and/or fish gelatins and mixtures thereof, preferably comprising at least one gelatin with a bloom value of greater than or equal to 200, preferably with a bloom value of greater than or equal to 240), maltodextrin (preferably obtained from maize (corn), wheat, tapioca or potato, preferred maltodextrins have a DE value of 10-20), modified cellulose (for example cellulose ether), alginates (for example Na-alginate), carrageenan (beta-, iota-, lambda- and/or kappa carrageenan), gum arabic, curdlan and/or agar-agar. Gelatin is preferably used, in particular, because of its good availability in different bloom values. Particularly preferred, especially for oral use are seamless gelatin or alginate capsules, the covering of which dissolves very rapidly in the mouth or bursts when chewing. Production may take place, for example, as described in EP 0389700 A1, U.S. Pat. Nos. 4,251,195, 6,214,376, WO 2003 055587 or WO 2004 050069 A1.

The capsules, however, may also represent micro-capsules. "Microcapsules" are understood to be spherical aggregates with a diameter of about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone.

Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

The active principles are released from the microcapsules by mechanical, thermal, chemical or enzymatic destruction of the membrane, normally during the use of the preparations containing the microcapsules. Despite the fact that the state of the art a huge range of possibilities for the encapsulation of actives, methods according to which a shell is obtained by coazervation, precipitation or polycondensation of anionic and cationic polymers has been quite suitable for the formation of stable capsules. Particularly, a preferred process for the encapsulation of active principles according to the present invention is characterised in that it comprises the steps of (a) preparing a matrix from gel formers, cationic polymers and active principles;

(b) optionally dispersing said matrix in an oil phase; and (c) treating said dispersed matrix with aqueous solutions of anionic polymers and optionally removing the in phase in the process.

Of course, anionic and cationic polymers in steps (a) and (c) can be exchanged.

(i) Gel formers. In the context of the invention, preferred gel formers are substances which are capable of forming gels in aqueous solution at temperatures above 40° C. Typical examples of such gel formers are heteropolysaccharides and proteins. Preferred thermogelling heteropolysaccharides are agaroses which may be present in the form of the agar agar obtainable from red algae, even together with up to 30% by weight of non-gel-forming agaropectins. The principal constituent of agaroses are linear polysaccharides of Galactose and 3,6-anhydro-L-galactose with alternate 1,3- and 1,4-glycosidic bonds. The heteropolysaccharides preferably have a molecular weight of 110,000 to 160,000 and are both odourless and tasteless. Suitable alternatives are pectins, xanthans (including xanthan gum) and mixtures thereof. Other preferred types are those which in 1% by weight aqueous solution still form gels that do not melt below 80° C. and solidify again above 40° C. Examples from the group of thermogelling proteins are the various gelatines.

(ii) Anionic polymers. Salts of alginic acid are preferred for this purpose. The alginic acid is a mixture of carboxyl-containing polysaccharides with the following idealized monomer unit:

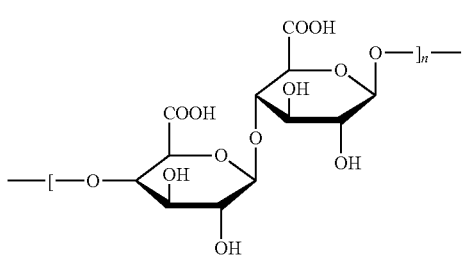

The average molecular weight of the alginic acid or the alginates is in the range from 150,000 to 250,000. Salts of alginic acid and complete and partial neutralization products thereof are understood In particular to be the alkali metal salts, preferably sodium alginate ("algin") and the ammonium and alkaline earth metal salts. Mixed alginates, for example sodium/magnesium or sodium/calcium alginates, are particularly preferred. In an alternative embodiment of the invention, however, carboxymethyl celluloses and anionic chitosan derivatives, for example the carboxylation and above all succinylation products are also suitable for this purpose.

(iii) Cationic polymers. Chitosans are biopolymers which belong to the group of hydrocolloids. Chemically, they are partly de-acetylated chitins differing in their molecular weights which contain the following—idealized—monomer unit:

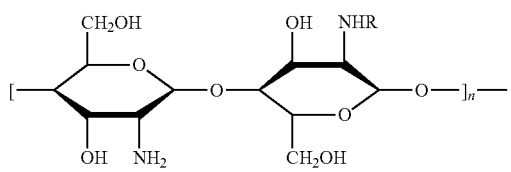

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations.

In a preferred embodiment of the invention a 1 to 10 and preferably 2 to 5% by weight aqueous solution of the gel former, preferably agar agar, is normally prepared and heated under reflux. A second aqueous solution containing the cationic polymer, preferably chitosan, in quantities of 0.1 to 2 and preferably 0.25 to 0.5% by weight and the active principle in quantities of 0.1 to 25 and preferably 0.25 to 10% by weight is added in the boiling heat, preferably at 80 to 100° C.; this mixture is called the matrix. Accordingly, the charging of the microcapsules with active principles may also comprise 0.1 to 25% by weight, based on the weight of the capsules. If desired, water-insoluble constituents, for example inorganic pigments, may also be added at this stage to adjust viscosity, generally in the form of aqueous or aqueous/alcoholic dispersions. In addition, to emulsify or disperse the active principles, it can be useful to add emulsifiers and/or solubilisers to the matrix. After its preparation from gel former, cationic polymer and active principle, the matrix optionally is very finely dispersed in an oil phase with intensive shearing in order to produce small particles in the subsequent encapsulation process. It has proved to be particularly advantageous in this regard to heat the matrix to temperatures in the range from 40 to 60° C. while the oil phase is cooled to 10 to 20° C. The actual encapsulation, i.e. formation of the membrane by contacting the cationic polymer in the matrix with the anionic polymers, takes place in the third step. To this end, it is advisable to wash the matrix—dispersed in the oil phase—with an aqueous ca. 0.1 to 3 and preferably 0.25 to 0.5% by weight aqueous solution of the anionic polymer, preferably the alginate, at a temperature in the range from 40 to 100 and preferably 50 to 60° C. and, at the same time, to remove the oil phase if present. The resulting aqueous preparations generally have a microcapsule content of 1 to 10% by weight. In some cases, it can be of advantage for the solution of the polymers to contain other ingredients, for example emulsifiers or preservatives. After filtration, microcapsules with a mean diameter of preferably 1 to 3 mm are obtained. It is advisable to sieve the capsules to ensure a uniform size distribution. The microcapsules thus obtained may have any shape within production-related limits, but are preferably substantially spherical.

The pharmaceutical and cosmetic compositions of the present invention are preferably dermatological compositions, which are preferably administered topically to the skin. Therefore, an object of the invention is a method for cosmetically affecting a skin care treatment comprising topically applying to the skin a skin care efficient amount of one or more of a compound of formula (I), respectively formula (II).

Another object of the invention is a method for the cosmetically treatment of the epidermis of human beings suffering from the signs of aging, suffering from dry skin and for the prevention of free radical formation on skin, comprising topically administering an effective amount of one or more compounds of formula (I)), respectively formula (II) to the epidermis.

In a further embodiment the present invention also refers to a process for preparing a cream, especially intended for topically treatment of skin to reduce signs of aging, reduce dry skin and maladies associated with free radical formation on skin, comprising blending one or more compounds of formula (I), respectively formula (II) with a cream base.

The term "cream base" means a basic formulation comprising ingredients, which are mentioned above, thus the formulation, can be used as cream or lotion or ointment.

Further, a process is preferred for the cosmetical or dermatological treatment of the skin, comprising applying a cosmetic or pharmaceutical composition of the present invention to the skin.

EXAMPLES

Preparation of Compounds of Formula (I), Respectively Formula (II)

Manufacturing of the Succinate Derivates
i) Method 1: N,N-Dimethyl-succinamic acid 3,3,5-trimethyl-cyclohexyl ester (S7): N,N-Dimethylsuccinamic acid
    160 g (1.60 Mol) of Succinic anhydride and 130 g (1.60 Mol) of Dimethylamine hydrochloride are suspended in 960 g of Ethyl acetate and heated to 50° C. under stirring and nitrogen atmosphere. Then 162 g (1.60 Mol) of Triethylamine are added within 4 h, stirring is continued for additional 1 h. During this dosage white crystals of the Triethyl amine hydrochloride precipitate.

Temperature is raised to 65° C. and the precipitation is filtered. The filtrate comprising the intermediate can be used for the next step.

a) 426 g (3,00 Mol) of Homomenthol is added to the above-mentioned filtrate, the temperature is raised to 60° C. and under stirring and a vacuum of 100 mbar the Ethyl acetate is distilled off the reaction mixture. Then 56 g of Sulfuric acid are added at a temperature of 50° C. within 20 minutes, stirring is continued for 6 h. For work-up 500 g of Toluene are added to the reaction mixture and after cooling to 5-10° C. the dosage of 500 g of iced water follows. After separation of the water layer the organic layer is washed to neutral with aqueous Sodium hydroxide solution (10% w/w) and finally with saturated aqueous Sodium chloride solution. After separation of the water layer the organic layer is distilled resulting 250 g (0,93 Mol) of product. Yield (overall): 58% of theory.

ii) Method 2: (1R,2S,5R)-2-isopropyl-5-methyl-cyclohexyl] 4-(diisopropylamino)-4-oxo-butanoate (S1):

a) N,N-Dimethylsuccinamic acid 160 g (1.60 Mol) of Succinic anhydride and 162 g (1.60 Mol) of Diisopropylamine are dissolved in 960 g of Ethyl acetate and heated to 50° C. under stirring and nitrogen atmosphere. Stirring is continued for additional 5 h. This solution comprising the intermediate can be used for the next step.

b) 468 g (3,00 Mol) of L-Menthol is added to the above-mentioned solution, the temperature is raised to 60° C. and under stirring and a vacuum of 100 mbar the Ethyl acetate is distilled off the reaction mixture. Then 56 g of Sulfuric acid are added at a temperature of 50° C. within 20 minutes, stirring is continued for 6 h. For work-up 500 g of Toluene are added to the reaction mixture and after cooling to 5-10° C. the dosage of 500 g of iced water follows. After separation of the water layer the organic layer is washed to neutral with aqueous Sodium hydroxide solution (10% w/w) and finally with saturated aqueous Sodium chloride solution. After separation of the water layer the organic layer is distilled resulting 200 g of product.

iii) Preparation of S2, S3, S4, S5, S6, S8, S9, S10:

a) N,N-diethyl succinic acid amid-3,3,5-trimethylcyclohexylester (S2):

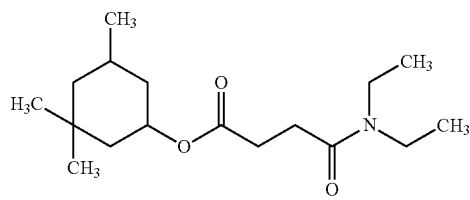

Preparation according to method 1 with diethylamine, Yield: 50%.

b) N,N-dimethyl succinic acid amid-2,3,6-trimethylcyclohexylester (S3):

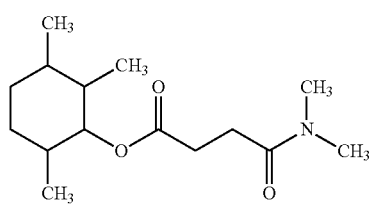 [SMILES: CC1CCC(C)C(OC(=O)CCC(=O)N(C)C)C1C]

Preparation according to method 1 with 2,3,6-trimethyl-cyclohexanol, Yield: 60%.

c) 3,3,5-trimethylcyclohexyl-N-ethylsuccimat (S4):

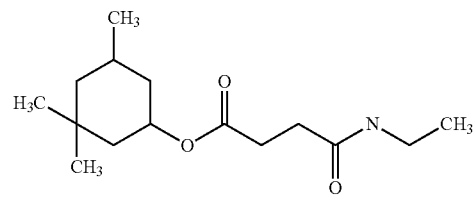 [SMILES: CCNC(=O)CCC(=O)OC1CC(C)CC(C)(C)C1]

Preparation according to method 1 with ethylamine hydrochloride, Yield: 40%.

d) 2-(isopropylcyclohexyl)4-(dimethylamino)-4-oxo-butanoate (S5):

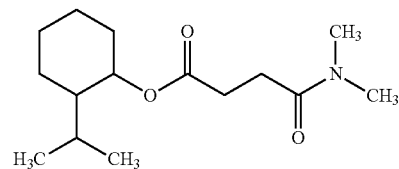 [SMILES: CC(C)C1CCCCC1OC(=O)CCC(=O)N(C)C]

Preparation according to method 1 with 2-isopropylcy-clohexanol, Yield: 55%.

e) (1R,2S,5R)-2-isopropyl-5-methyl-cyclohexyl]4-amino-4-oxo-butanoate (S6)

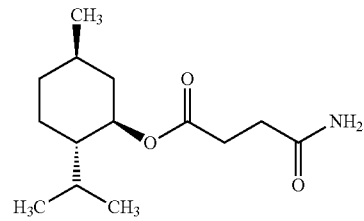 [SMILES: CC(C)[C@@H]1CC[C@@H](C)C[C@H]1OC(=O)CCC(N)=O]

Preparation according to method 1 with ammonium hydrochloride, Yield: 50%.

f) (3,3,5)-trimethylcyclohexyl)4-oxo-4-(1-piperidyl)butanoate (S8):

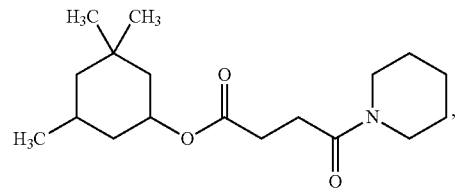 [SMILES: CC1CC(OC(=O)CCC(=O)N2CCCCC2)CC(C)(C)C1]

Preparation according to method 2 with piperidin, Yield: 55%.

g) 3,3,5-trimethylcyclohexyl)3-(dimethylamino)-3-oxo-propanoate (S9):

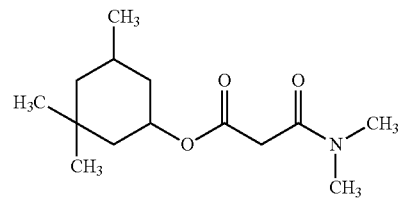

In analogy to above-mentioned procedure ethyl malonyl chloride reacts with dimethylamine in THF and the resulting intermediate is transferred through transesterification with homomenthol under catalysis of sodium methylate to the end-product. Yield: 40%.

h) 3,3,5-trimethylcyclohexyl)5-(dimethylamino)-5-oxo-pentanoate (S10):

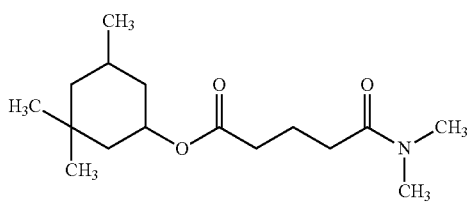

Preparation according to method 1 with glutaric anhydride. Yield: 60%.

Example 1

Cellular in vitro 20S Proteasome Assay on Normal Human Dermal Fibroblasts (NHDF)

NHDF (normal human dermal fibroblasts) cells are disseminated in a 96-well microtiter plate in a concentration of 1×105 cells/well (DMEM, 10% FCS). After cultivation for 24 h at 37° C. and 5% CO2 in DMEM medium, enriched with 10% FCS, various concentrations of the test substances and are added and incubated for a further 72 h. The maximum concentration of the test substances used corresponds from 0.3 times of the IC20 value of the cytotoxicity assay. The 20S Proteasome Assay (AAT Bioquest, Inc.) is performed according to the manufacturer's protocol. The Amplite™ Flourometric 20S Proteasome Assay Kit is a homogenous fluorescent assay that measures the chymotrypsin-like protease activity associated with the proteasome complex. This kit uses LLVY_R110 as a flourogenic indicator for proteasome activity. Cleavage of LLVY-R110 by proteasome generates the strongly green fluorescent R110 that is monitored fluorometrically. The fluorescence of the blank wells with growth medium was subtracted from the value for those wells with the cells. The results of the cells with treatment with different substances were compared with untreated cells.

TABLE 1

20S proteasome stimulation relative to control

| Substance | Concentration [mM] | Stimulation [%] ± SD [%] |
|---|---|---|
| Control* | 0.006 | 110 |
| S1 | 0.327 | 208 |
| S2 | 0.460 | 154 |
| S3 | 1.060 | 166 |
| S4 | 2.910 | 141 |
| S5 | 0.880 | 176 |
| S6 | 0.750 | 170 |
| S7a | 0.324 | 170 |
| S7b | 0.114 | 228 |
| S7a/S7b** | 3.240 | 216 |
| S7a/S7b** | 1.140 | 190 |
| S7a/S7b** | 0.324 | 148 |
| S7a/S7b** | 0.114 | 133 |
| S8 | 5.000 | 125 |
| V9 | 15.00 | 160 |
| V10 | 15.00 | 146 |

*Resveratrol
**ratio trans:cis = 1:4

Example 2

Cellular in vitro Stem Cell Protection Assay on HHFSC (Human Hair Follicle Stem Cells)

HHFSC (Human Hair Follicle Stem Cells) isolated from hair follicle bulge (Celprogen) were cultivated in culture ware pre-coated with Human Hair Follicle Stem Cell Extracellular Matrix (Celprogen). The cells were incubated 2 h prior to and 16 h after UVB irradiation with test compounds. Cells were irradiated with 25 mJ/cm$^2$ UVB in the presence of buffer solution. Apoptosis induction was evaluated by caspase 3/7 protein expression (Caspase-Glo 3/7, Promega) and quantified by chemiluminescence measurement.

The inhibition of apoptosis induction in the presence of test substances was calculated according to the following equation:

$$\text{Inhibition of apoptosis induction [\%]} = 100 - \left( \frac{RLU \text{ test substance} - RLU \text{ control without } UVB}{RLU \text{ control} - RLU \text{ control without } UVB} \times 100 \right)$$

The abbreviations have the following meanings:
RLU test substance:
  RLU of the wells with test substance and with UVB irradiation
RLU control:
  RLU of the wells without test substance, but with UVB irradiation
RLU control without UVB:
  RLU of the wells without test substance and without UVB irradiation

TABLE 2

Inhibition of apoptosis induction relative to control

| Substance | Concentration [mM] | Inhibition of UV induced apoptosis [%] |
|---|---|---|
| UVB-irradiation = positive control | 25 mJ/cm$^2$ | -/- |
| S7a/S7b** | 0.02 mM | 5 |
| S7a/S7b** | 0.20 mM | 32 |

**ratio trans:cis = 1:4

Example 3

Cellular in vitro DCF Assay Stem Cell on Primary Human Dermal Fibroblasts (Lonza)

DCF Assay (in vitro)

Primary human dermal fibroblasts (Lonza) are disseminated in a 96-well microtiter plate in a concentration of 1×104 cells/well (DMEM, 10% FKS). After cultivation in fully enriched medium (DMEM, 10% FCS) for 24 h at 37° C. and 5% CO2, the serum content was reduced to 0.1% for further 24 h to synchronize the cell cycle. Confluence was supposed to be around 70% at the time, the incubation with the test substances began. Various concentrations of the test substances, two backgrounds (untreated cells), control (possible with solvent) and Trolox as internal standard (1000 µM) were applied to the cells in DMEM and incubated for further 18-20 h. After 24 h of incubation, 100 µl H2DCF-DA-solution (2,7-Dichlorfluorescein, 10 µM) incl. DAPI (1:1000) was added to all samples (excluded the background-control) and incubated for one hour to de-esterify the H2DCF-DA by cellular esterases. The resulting H2DCF was thereby trapped inside the cell. After the incubation, the cells were washed and the prooxidant challenge was set (1 mM, 1 h). The resulting fluorescence was read at Ex 504 nm; Em 524 nm. An increased level of ROS (reactive oxygen species) led to an increased amount of fluorescence.

Results are mean values from 2 independent experiments with quadruple determinations each.

The inhibition of the oxidation in the presence of test substances was calculated according to the following equation:

The abbreviations have the following meanings:
RFU DAPI: Relative fluorescence units (Ex 380/20, Em 440/40) of the wells with test substance, DAPI and DCF treatment, with cells
RFU DCF: Relative fluorescence units (Ex 485/20, Em 528/20) of the wells with test substance, DAPI and DCF treatment, with cells
RFU control: Relative fluorescence units of the wells without test substance, DAPI and DCF treatment, with cells (The control was calculated like the other samples.)
RFU BLANK: Relative fluorescence units of the wells without test substance, without DAPI and DCF treatment but with cells

TABLE 3

Activity based on the inhibition of oxidation

| Substance | Concentration mM | Intracellular ROS reduction [%] |
|---|---|---|
| S7a/S7b** | 0 | 0 |
| S7a/S7b** | 1 | −2 |
| S7a/S7b** | 10 | 11 |
| S7a/S7b** | 50 | 16.3 |
| S7a/S7b** | 100 | 19.5 |

**ratio trans:cis = 1:4

Example 4

Cellular in vitro Heme Oxygenase-1 Expression Assay on Normal Human Dermal Fibroblast Cells (NHDF)

NHDF (normal human dermal fibroblasts) cells were disseminated in a 6-well plate in a concentration of $2 \times 10^5$ cells/well (DMEM, 10% FCS). After cultivation in fully enriched medium (DMEM, 10% FCS) for 72 h at 37° C. and 5% CO2, the serum content was reduced to 0.1% to synchronize the cell cycle. Various concentrations of the test substances, the negative control (untreated cells) and tert. butylhydrochinon as positive control, are added and incubated for a further 24 h. The maximum concentration of the test substances used corresponds to 0.2 times the value of the IC20 of the cytotoxicity assay. After cell lysis, the protein amount was determined using the Biorad BCA assay. All samples were adjusted to the same protein level before application on a fast Criterion Gel (Biorad) to perform electrophoresis for 20 minutes at 300 V. Thereafter the proteins were transferred to a PVDF membrane on a semi-dry blotter (30 minutes, 25 V). The blotted membrane is blocked for 4 hours in a 5% milk powder solution in TBST at 4° C. After washing, the membrane is incubated with the first antibody solution HO-1 from abcam (1:500 in 1% milk powder in TBST) over night. After this, washing is repeated and the membrane has to be incubated for 1 h in the second antibody solution (goat anti mouse coupled to HRP; 1:800 in 1% milk powder). After washing, the membrane is exposed to chemiluminescence HRP-substrate solution for 5 minutes. The resulting band pattern is detected with a chemiluminescence sensitive camera system (Vil-ber Loumat). The quantification was done by densitometry, using the Image J freeware software.

TABLE 4

Upregulation of HO1-Amount relative to control

| Substance | Concentration [% b.w.] | Up-regulation |
|---|---|---|
| S7a/S7b** | 0.0134% | 14.5-fold |

**ratio trans:cis = 1:4

Example 5

Cellular in vitro Hyaluronic Acid Assay on Normal Human Dermal Fibroblasts (NHDF)

NHDF (normal human dermal fibroblasts) cells were disseminated in a 96-well microtiter plate in a concentration of $2 \times 10^4$ cells/well (DMEM, 10% FCS). After cultivation in fully enriched medium (DMEM, 10% FCS) for 72 h at 37° C. and 5% CO2, the serum content was reduced to 0.1% to synchronize the cell cycle and incubated for further 24 h. Various concentrations of the test substances and TGF-beta1 as internal standard are added and incubated for 72 h. The maximum concentration of the test substances used corresponds to 0.2 times the value of the IC20 of the cytotoxicity assay. Hyaluronic acid is quantified by a competitive ELISA (TECOmedical TE1017).

The percent bound for each standard and unknown substance is calculated using the following equation:

$$x = \left( \frac{\left( \frac{1}{RFU_{(sample)}} \right) - b}{m} \right) * \text{dilution}$$

The abbreviations have the following meanings
RFU (standard or test substance): Absorption of the wells with standard or test substance
m and b values from the standard curve y=mx+b
A standard curve is generated by plotting the aborptions of the given concentrations in a linear proportion. The gradient of the line is determined and the value of the substances calculated as follows:
1. value=1/RFU
2. value=((1. value)−b)/m)
Compound of Hyaluronic acid [ng/ml]=2. value*dilution

TABLE 5

Hyaluronic acid stimulation relative to control

| Substance | Concentration [% b.w.] | Stimulation |
|---|---|---|
| S7a/S7b** | 0.00120 | 67.3% |
| S7a/S7b** | 0.00012 | 34.4% |

**ratio trans:cis = 1:4

Example 6

Depigmentation Effect on Melanoma Cell Cultures

B16V mouse melanoma cells are disseminated in a 96-well micro-titre plate in a concentration of $7.5 \times 10^3$ cells/well. After cultivation for 24 h at 37° C. and 5% CO2 in RPMI medium, enriched with 10% foetal calf serum, various concentrations of the test substances and 0.6 mM tyrosine and 10 nM-MSH (-melanocyte stimulating hormone) are added and incubated for a further 96 h. The maximum concentration of the test substances used corresponds to 0.1 times the value of the $IC_{20}$ value of the cytotoxicity assay. Only tyrosine and -MSH are added to the controls. After incubation, sodium hydroxide solution (final concentrations: 1 M) is added to the culture medium and the absorption (A) is measured after 3 h at 400 nm.

The inhibition of pigmentation in the presence of the test compounds was calculated using the following equation:

Inhibition of pigmentation (%)=100−[($A_{test\ compound}$/$A_{control}$)×100]

wherein
$A_{test\ compound}$=absorption of the wells with test substance and with cells
$A_{control}$=absorption of the wells without test substance, but with cells From the inhibition of pigmentation (%) in a series of dilutions of test compounds, the $IC_{50}$ for each test compound is calculated. This is the concentration of a test compound at which pigmentation is inhibited by 50%.

TABLE 6

| Inhibition of pigmentation | |
|---|---|
| Substance | $IC_{50}$ [μM] |
| Control*** | 452.3 |
| S7a/S7b** | 18.4 |

**ratio trans:cis = 1:4
***Kojic acid

Examples 7-18

Skin and Hair Care Products

7=Skin-lightening day care fluid O/W
8=Shaving Cream O/W
9=After shave hydro gel
10=After-Sun spray O/W
11=Sunscreen lotion (O/W), broad-band protection
12=W/O night cream
13=Barrier repair cream O/W
14=Calming Balm
15=Antiperspirant pump spray
16=Body Wash
17=Body Oil
18=Anti-Cellulite Balm
whereby S7a/S7b is  ratio trans:cis=1:4

| Raw Material | | | % | | | | | | | | | | | |
|---|---|---|---|---|---|---|---|---|---|---|---|---|---|---|
| Name Manufacturer | INCI | 7 | 8 | 9 | 10 | 11 | 12 | 13 | 14 | 15 | 16 | 17 | 18 |
| S7a/S7b** | | 0.05–0.5 | 0.05–0.5 | 0.05–0.5 | 0.05–0.5 | 0.05–0.5 | 0.05–0.5 | 0.05–0.5 | 0.05–0.5 | 0.05–0.5 | 0.05–0.5 | 0.05–0.5 | 0.05–0.5 |
| –(-Alpha-)-Bisabolol, natural (Symrise) | Bisabolol | | 0.4 | | | | | | | 0.1 | | | 0.1 |
| Abil 350 (Degussa-Goldschmidt) | Dimethicone | 0.5 | | | | | 0.5 | 2.0 | | | | | 3.0 |
| Allantoin (Merck) | Allantoin | | | | 0.1 | | | | | 0.1 | | | |
| Aloe Vera Gel Concentrate 10/1 (Symrise) | Water (Aqua), Aloe Barbadensis Leaf Juice | | | | 1.0 | | 3.0 | | | | | | |
| Alugel 34 TH (Baerlocher) | Aluminium Stearate | | | | | | 1.0 | | | | | | |
| Arbutin (Sabinsa) | beta-Arbutin | 1.0 | | | | | | | | | | | |
| Arylpon F (Cognis) | Laureth-2 | | | | | | | | | | | | |
| Avocado Oil (Symrise) | Persea Gratissima (Avocado) Oil | | | | 3.0 | | | | | | | 2.0 | |
| Caffeine pure | Caffeine | | | | | | | | | | | | 1.0 |
| Carbopol ETD 2050 (Noveon) | Carbomer | 0.2 | | | | | 0.2 | | | | | | |
| Carbopol Ultrez 21 (Noveon) | Acrylates/C10-30 Alkyl Acrylate Crosspolymer | | | | 0.4 | | | | | 0.6 | | | |
| CeramideBio (Symrise) | Cetylhydroxyproline Palmitamide | | | | | | | | 0.5 | | | | |
| Ceramide SL (Sino Lion) | Hydroxyethyl Palmityl Oxyhydroxypropyl Palmitamide | | | | | | | 0.1 | | | | | |
| Citric Acid 10% sol. | Citric Acid | | | | | | | | | | | 0.3 | 0.2 |

-continued

| Raw Material Name Manufacturer | INCI | % | | | | | | | | | | | |
|---|---|---|---|---|---|---|---|---|---|---|---|---|---|
| | | 7 | 8 | 9 | 10 | 11 | 12 | 13 | 14 | 15 | 16 | 17 | 18 |
| Comperlan 100 (BASF) | Cocamide MEA | | | | | | | | | | 0.5 | | |
| Covi-Ox T-70 (Cognis) | Tocopherol | | | | 0.1 | | | | | | | 0.2 | |
| Crinipan AD (Symrise) | Climbazole | | | | | | | | | | | | |
| Dehyquart A CA (Cognis) | Cetrimonium Chloride | | | | | | | | | | | | |
| Dow Corning 246 Fluid (Dow Corning) | Cyclohexasiloxane, Cyclopentasiloxane | | | | | 2.0 | 2.0 | | | | | | |
| D-Panthenol (BASF) | Panthenol | | | | 0.5 | 1.0 | | | 1.0 | | | | |
| Dracorin CE (Symrise) | Glyceryl Stearate Citrate | | | | | | | | 1.5 | | | | |
| Dracorin GMS (Symrise) | Glyceryl Stearate | | | | | | | | 2.0 | | | | |
| Dracorin GOC (Symrise) | Glyceryl Oleate Citrate, Caprylic/Capric Triglyceride | | | | 2.0 | | | | | | | | |
| Dragocid Liquid (Symrise) | Phenoxyethanol, Methylparaben, Ethylparaben, Butylparaben, Propylparaben, Isobutylparaben | 0.8 | | | | 0.7 | 0.8 | 0.8 | | | | | 0.4 |
| Dragoderm (Symrise) | Glycerin, Triticum Vulgare (Wheat) Gluten, Water (Aqua) | | | | | | | | | | 1.0 | | |
| Dragosan W/O Liquid (Symrise) | Polyglyceryl-3-Polyricinoleate, Sorbitan Isostearate | | | | | | 1.0 | | | | | | |
| Dragosan W/O P (Symrise) | Sorbitan Isostearate, Hydrogenated Castor Oil, Ceresin, Beeswax (Cera Alba) | | | | | | | | 6.0 | | | | |
| Dragosantol 100 (Symrise) | Bisabolol | 0.2 | | | | | | | | | | | |
| Dragoxat 89 (Symrise) | Ethylhexyl Ethylisononanoate | | | | | | | | 2.0 | | | 10.0 | |
| Edenor L2 SM (Cognis) | Stearic Acid, Palmitic Acid | | 24.0 | | | | | | | | | | |
| Edenor K 12-18 (Cognis) | Coconut-Palmkernel Oil Fatty Acid | | 10.0 | | | | | | | | | | |
| EDTA B Powder (BASF) | Tetrasodium EDTA | | 0.2 | | | | | | | | | | |
| Edeta BD (BASF) | Disodium EDTA | 0.1 | | | | 0.1 | | | 0.1 | | 0.1 | | |
| Emulsiphos (Symrise) | Potassium Cetyl Phosphate, Hydrogenated Palm Glycerides | 1.5 | | | | 1.5 | | 2.0 | | | | | |
| Ethanol 96% | Alcohol Denat. | | | 8.0 | 5.0 | | | | | | | | |
| Extrapone Guarana (Symrise) | Water (Aqua), Propylene Glycol, Paullinia Cupana Seed Extract, Alcohol | | | | | | | | | | 1.0 | | |

| Raw Material Name Manufacturer | INCI | 7 | 8 | 9 | 10 | 11 | 12 | 13 | 14 | 15 | 16 | 17 | 18 |
|---|---|---|---|---|---|---|---|---|---|---|---|---|---|
| Extrapone Witch Hazel Distillate colourless (Symrise) | Propylene Glycol, Hamamelis Virginiana (Witch Hazel) Water, Water (Aqua), Hamamelis Virginiana (Witch Hazel) Extract | | | | | | 1.0 | | 0.2 | | | | |
| Extrapone Rosemary GW (Symrise) | Glycerin, Water (Aqua), Rosmarinus officinalis (Rosemary) Leaf Extract | | | | | | | 0.5 | | | | | |
| Extrapone Seaweed (Symrise) | Water (Aqua), Propylene Glycol, Potassium Iodide, Fucus Vesiculosus Extract | | | | | | | | | | | | 2.5 |
| Fragrance PFO1 or PFO2 (Symrise) | Fragrance | 0.3 | 1.0 | 0.1 | 0.25 | 0.4 | 0.4 | 0.3 | 0.2 | 1.0 | 0.5 | 0.5 | 0.4 |
| Frescolat MGA (Symrise) | Menthone Glycerin Acetal | | 0.5 | | | | | | | | | | |
| Frescolat ML cryst. (Symrise) | Menthyl Lactate | | | 0.3 | 0.5 | | | | | | | | |
| Genapol LRO liquid (Cognis) | Sodium Laureth Sulfate | | | | | | | | | | 37.0 | | |
| Givobio GZN (Seppic) | Zinc Gluconate | | | | | | | 0.5 | | | | | |
| Glycerol 85% | Glycerin | 3.5 | 2.3 | | 4.7 | 4.7 | 2.0 | 3.0 | 1.7 | | | | |
| Hydrolite-5 (Symrise) | Pentylene Glycol | | | 5.0 | 5.0 | | | | 3.0 | 5.0 | | | |
| Hydroviton 24 (Symrise) | Water, Pentylene Glycol, Glycerin, Sodium Lactate, Lactic Acid, Serine, Urea, Sorbitol, Sodium Chloride, Allantoin | | | | | | | | 1.0 | | 1.0 | | |
| Isoadipate (Symrise) | Diisopropyl Adipate | 2.0 | | | | | | | | | | | |
| Isodragol (Symrise) | Triisononanoin | | | | | | | | 3.0 | 1.0 | | 10.0 | |
| Karion F (Merck) | Sorbitol | | | | | | 2.0 | | | | | | |
| Keltrol T (Danby-Chemie) | Xanthan Gum | 0.2 | | | | 0.2 | | | | | | | |
| Kojic acid (Cosmetochem) | Kojic Acid | 0.5 | | | | | | | | | | | |
| Lanette 16 (Cognis) | Cetyl Alcohol | 1.5 | | | | | | | | | | | |
| Lanette O (Cognis) | Cetearyl Alcohol | | | | | | 1.0 | | 2.0 | | | | |
| Locron L (Cognis) | Aluminium Chlorohydrate | | | | | | | | | | 16.0 | | |
| Macadamia Nut Oil | Macadamia Ternifoia Seed Oil | | | | | | | | | | | 0.5 | |
| Magnesium Chloride (Merck) | Magnesium Chloride | | | | | | 0.7 | | | | | | |
| Merquat 550 (Lubrizol) | Polyquaternium-7 | | | | | | | | | | 0.5 | | |
| Mineral Oil | Paraffinum Liquidum | | | | | | | | | | | 49.6 | |

-continued

| Raw Material Name Manufacturer | INCI | % | | | | | | | | | | | |
|---|---|---|---|---|---|---|---|---|---|---|---|---|---|
| | | 7 | 8 | 9 | 10 | 11 | 12 | 13 | 14 | 15 | 16 | 17 | 18 |
| Neo Heliopan 357 (Symrise) | Butyl Methoxy-dibenzoyl-methane | 2.0 | | | | 1.0 | | | | | | | |
| Neo Heliopan AP (Symrise) (10% as sodium salt) | Disodium Phenyl Dibenzimidazole Tetrasulfonate | | | | | 10.0 | | | | | | | |
| Neo Heliopan AV (Symrise) | Ethylhexyl Methoxy-cinnamate | 7.5 | | | | 3.0 | | | | | | | |
| Neo Heliopan BB (Symrise) | Benzophenone-3 | 3.0 | | | | | | | | | | | |
| Neo Heliopan Hydro (Symrise) (15% as sodium salt) | Phenylbenz-imidazole Sulfonic Acid | | | | | 6.7 | | | | | | | |
| Neo Heliopan HMS (Symrise) | Homosalate | 10.0 | | | | | | | | | | | |
| Neo Heliopan MBC (Symrise) | 4-Methylbenzylidene Camphor | | | | | 1.5 | | | | | | | |
| Neo Heliopan OS (Symrise) | Ethylhexyl Salicylate | 5.0 | | | | 5.0 | | | | | | | |
| Neo-PCL Water Soluble N (Symrise) | Trideceth-9, PEG-5 Ethylhexanoate, Water (Aqua) | | | 1.0 | | | | | | 2.0 | | | |
| Neutral Oil | Caprylic/Capric Triglyceride | | 3.0 | | 5.0 | 2.0 | | 10.0 | | | | | |
| Oxynex 2004 (Merck) | BHT | | | | | | 0.1 | | | | | | |
| Oxynex ST Liquid (Merck) | Diethylhexyl Syringylidene Malonate) | | | | | | | 0.5 | | | | | |
| Oxypon 328 (Zschimmer & Schwarz) | Peg-26 Jojoba Acid, Peg-26 Jojoba Alcohol | | | | | | | | | | | | 1.0 |
| PCL Liquid 100 (Symrise) | Cetearyl Ethylhexoate | | | | 4.0 | | | | 3.0 | | 21.0 | | |
| PCL Solid (Symrise) | Stearyl Heptanoate, Stearyl Caprylate | | | | 0.5 | | | | 1.0 | | | | |
| PCL Liquid (Symrise) | Cetearyl Ethylhexanoate, Isopropyl Myristate | | | | | | 12.0 | | | | | | |
| Pemulen TR-2 (Noveon) | Acrylates/C10-30 Alkyl Acrylate Crosspolymer | | | | 0.25 | | | | | | | | |
| Phytoconcentrole Shea Butter (Symrise) | *Glycine Soja* (Soybean) Oil, *Butyrospermum Parkii* (Shea Butter) | | | | | | | | | | | 0.5 | |
| Polymer JR 400 (Nordmann, Rassmann) | Polyquaternium-10 | | | | | | | | | | | | |
| Polyquart H 81 (Cognis) | PEG-15 Coco Polyamine | | | | | | | | | | | | |
| Potassium Hydroxide 50% Solution | Potassium Hydroxide | | | 11.0 | | | | | | | | | |
| Potassium Sorbate | Potassium Sorbate | | | | | 0.1 | | | | | | | |
| Propylene Glycol-1,2 99 | Propylene Glycol | | | 5.0 | | | | | | 3.0 | | | 2.0 |
| Retinyl Palmitate in Oil (DSM Nutrional Products) | Retinyl Palmitate | | | | | | 0.2 | | | | | 0.05 | |

-continued

| Raw Material Name Manufacturer | INCI | % |||||||||||| 
|---|---|---|---|---|---|---|---|---|---|---|---|---|---|
| | | 7 | 8 | 9 | 10 | 11 | 12 | 13 | 14 | 15 | 16 | 17 | 18 |
| Sepigel 305 | Polyacrylamide C13-14 Isoparaffin, Laureth-7 | | | | | | | | | | | | 2.0 |
| Sodium Ascorbyl Phosphate (EMD Chemicals) | Sodium Ascorbyl Phosphate | 1.0 | | | | | | | | | | | |
| Sodium Benzoate | Sodium Benzoate | | | | | | | | | | 0.5 | | |
| Sodium Chloride | Sodium Chloride | | | | | | | | | | 1.0 | | |
| Sodium Hydroxide 50% Solution | Sodium Hydroxide | | | 1.0 | | | | | | | | | |
| Sodium Hydroxide 10% Solution | Sodium Hydroxide | 0.2 | | 0.7 | | | | 0.3 | 1.0 | | | | |
| Solubilizer (Symrise) | PEG-40 Hydrogenated Castor Oil, Trideceth-9, Water (Aqua) | | | 1.5 | | | | | | 3.0 | | | |
| Sun Flower Oil (Wagner) | Helianthus Annuus (Sunflower) Seed Oil | | | | | | 5.0 | | | | | | |
| Sweet Almond Oil (Wagner) | Prunus dulcis | | | | | | 5.0 | | | | | | |
| Sym3D (Symrise) | Hydroxymethoxyphenyl Propylmethylmethoxybenzofuran | | | | | | 0.25 | | | | | | |
| SymCalmin (Symrise) | Butylene Glycol, Pentylene Glycol, Hydroxy phenyl Propamidobenzoic Acid | | | | 0.2 | | | | 1.0 | | | | |
| SymClariol (Symrise) | Decylene Glycol | | | | | | | | | | | | |
| SymDeo MPP (Symrise) | Dimethyl Phenyl 2-Butanol | | | | | | | | | 0.5 | | | |
| Symdiol 68 (Symrise) | 1,2-Hexanediol, Caprylyl Glycerol | | | | | | | | 1.0 | | | 1.0 | |
| SymFit 1617 (Symrise) | Trimethylcyclohexyl Butylcarbamate | | | | | | | | | | | | 0.1 |
| SymGlucan (ymrise) | Water (Aqua), Glycerin, Beta-Glucan | | | | 1.0 | | | | | | | | |
| SymHelios (Symrise) | Benzylidene Dimethoxydimethylindanone | | | | | 0.1 | | | | | | | |
| SymMatrix (Symrise) | Maltodextrin, Rubus Fruticosus (Blackberry) Leaf Extract | | | | | 0.2 | 1.0 | | | | | | |
| SymMollient W/S (Symrise) | Trideceth-9, PEG-5 Isononanoate, Water (Aqua) | | | | | | | | | | 1.0 | | |
| SymOcide PS (Symrise) | Phenoxyethanol, Decylene Glycol, 1,2-Hexanediol | | | | | | | | | | | | |
| SymPeptide 222 (Symrise) | Glycerin, Water (Aqua), Myristoyl Pentapeptide-8 | | | | | | | | | | | | 5.0 |

-continued

| Raw Material Name Manufacturer | INCI | % 7 | 8 | 9 | 10 | 11 | 12 | 13 | 14 | 15 | 16 | 17 | 18 |
|---|---|---|---|---|---|---|---|---|---|---|---|---|---|
| SymRelief 100 (Symrise) | Bisabolol, *Zingiber Officinale* (Ginger) Root Extract | | | | | | | | | | | 0.1 | |
| SymRelief S (Symrise) | Bisabolol, Hydroxymethoxyphenyl Decanone | | | 0.1 | 0.1 | | | | | | | | |
| SymRepair (Symrise) | Hexyldecanol, Bisabolol, Cetylhydroxy-proline Palmitamide, Stearic Acid, *Brassica Campestris* (Rapeseed) Sterols | | | | | | | | | | | 1.0 | |
| SymVital (Symrise) | *Aloe Barbadensis* leaf juice powder, Magnesium Ascorbyl Phosphate, *Rubus Idaeus* (Raspberry) Leaf Extract | | | | 0.1 | | | | | | | | 0.5 |
| SymWhite 377 (Symrise) | Phenylethyl Resorcinol | 0.5 | | | | | | | | | | | |
| Talcum | Talc | | | | | | | | | | | | 3.0 |
| Tamasterol (Tama Biochemicals) | Phytosterols | | | | | | | 0.3 | | | | | |
| Tego Betain L7 (Degussa) | Cocamidopropyl Betaine | | | | | | | | | | 6.0 | | |
| Tegosoft PC 31(Degussa) | | | | | | | | 0.3 | | | | | |
| Tegosoft TN (Degussa) | C12-15 Alkyl Benzoate | | | | | 5.0 | | | | | | | |
| Triethanolamine, 99% | Triethanol-amine | | | | 0.3 | 0.5 | | | | | | | |
| Tocopherol Acetate (DSM Nutritional Products) | Tocopheryl Acetate | | | | | 0.5 | 3.0 | 0.3 | | | | 0.5 | |
| Water, demineralized | Water (Aqua) | | | | | | Ad 100 | | | | | | |

The invention claimed is:

1. A cosmetic or pharmaceutical composition, comprising
(a) a compound of formula (I):

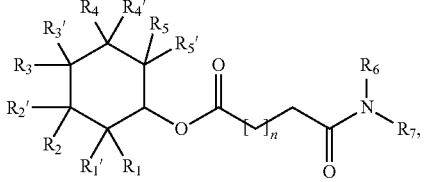

wherein $R_1$, $R'_1$, $R_2$, $R'_2$, $R_3$, $R'_3$, $R_4$ $R'_4$, $R_5$, $R'_5$, $R_6$, $R_7$ are independently of one another and denote hydrogen, hydroxyl, $C_1$ to $C_6$-alkyl group or $R_6$ and $R_7$ form together a C5-C6 ring system, n=0, 1, 2, 3, or 4, and selected from the group consisting of:
N,N-diethyl succinic acid amid -3,3,5-trimethylcyclohexylester (S2),
N,N-dimethyl succinic acid amid -2,3,6-trimethylcyclohexylester (S3),
3,3,5-trimethylcyclohexyl-N-ethylsuccimat (S4),
2-(isopropylcyclohexyl) 4-(dimethylamino)-4-oxo-butanoate (S5),
N,N-dimethyl-succinamic acid 3,3,5-trimethyl-cyclohexyl ester (S7),
(3,3,5)-trimethylcyclohexyl) 4-oxo-4-(1-piperidyl)butanoate (S8),
3,3,5-trimethylcyclohexyl) 3-(dimethylamino)-3-oxo-propancate (S9),
3,3,5-trimethylcyclohexyl) 5-(dimethylamino)-5-oxo-pentanoate (S10),
(b) at least one cosmetic or pharmaceutical additive, and
(c) at least one cosmetically acceptable carrier or at least one pharmaceutically acceptable carrier.

2. The composition according to claim 1, which is a composition for treatment of cellular ageing and cell life span, for treatment of free-radical activity, in a form for regulating renewal and differentiation of keratinocytes, for improving functional condition of skin or maintaining skin in good functional condition, for protecting skin or treating dry skin.

3. A method for the cosmetic treatment of anti-aging, delaying aging, toning, moisturizing and/or whitening, comprising applying a compound of formula (I):

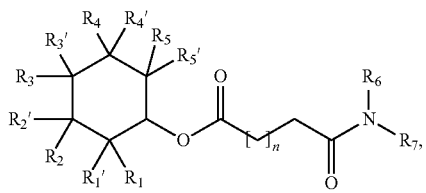

wherein $R_1$, $R'_1$, $R_2$, $R'_2$, $R_3$, $R'_3$, $R_4$ $R'_4$, $R_5$, $R'_5$, $R_6$, $R_7$ are independently of one another and denote hydrogen, hydroxyl, $C_1$ to $C_6$-alkyl group or $R_6$ and $R_7$ form together a C5-C6 ring system, n=0, 1, 2, 3, or 4, and selected from the group consisting of:
N,N-diethyl succinic acid amid -3,3,5-trimethylcyclohexylester (S2),
N,N-dimethyl succinic acid amid -2,3,6-trimethylcyclohexylester (S3),
3,3,5-trimethylcyclohexyl-N-ethylsuccimat (S4),
2-(isopropylcyclohexyl) 4-(dimethylamino)-4-oxo-butanoate (S5),
N,N-dimethyl-succinamic acid 3,3,5-trimethyl-cyclohexyl ester (S7),
(3,3,5)-trimethylcyclohexyl) 4-oxo-4-(1-piperidyl)butanoate (S8),
3,3,5-trimethylcyclohexyl) 3-(dimethylamino)-3-oxo-propanoate (S9),
3,3,5-trimethylcyclonexyl) 5-(dimethylamino)-5-oxo-pentanoate (S10).

4. The method according to claim 3, comprising activation and/or reactivation and/or protection of proteasome in nucleus and cytoplasm in eukaryotes.

5. The method according to claim 3, wherein the one or more compounds of formula (I) have an anti-free-radical activity, thus regulating the renewal and differentiation of the keratinocytes, for improving the functional condition of the skin or keeping the skin in good functional condition, for skin protection or treating dry skin.

6. A composition according to claim 1, wherein the cosmetic or pharmaceutical additives are selected from the group consisting of surfactants, oil bodies, emulsifiers, superfatting agents, pearlising waxes, consistency factors, polymers, silicone compounds, waxes, stabilizers, antidandruff agents, film formers, swelling agents, hydrotropes, preservatives, solubilizers, complexing agents, reducing agents, alkalising agents, perfume oils, dyes, thickeners, fats, lecithins, phospholipids, UV protection factors, moisturizers, biogenic agents, antioxidants, deodorants, antiperspirants, insect repellants, self-tanning agents, tyrosine inhibitors, and mixtures thereof.

7. A method for cosmetically affecting a skin care treatment comprising topically applying to the skin, a skin care efficient amount of a composition according to claim 1.

8. A method for the cosmetic treatment of the epidermis of human beings suffering from the signs of aging, suffering from dry skin and for the prevention of free radical formation on skin, comprising topically administering an effective amount of the composition according to claim 1 to the epidermis.

9. A process for preparing a cream, comprising blending one or more compounds of formula (I):

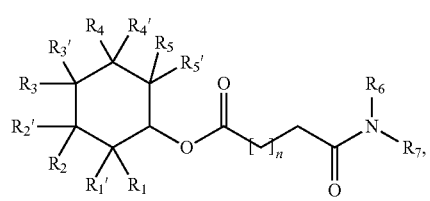

wherein $R_1$, $R'_1$, $R_2$, $R'_2$, $R_3$, $R'_3$, $R_4$ $R'_4$, $R_5$, $R'_5$, $R_6$, $R_7$ are independently of one another and denote hydrogen, hydroxyl, $C_1$ to $C_6$-alkyl group or $R_6$ and $R_7$ form together a C5-C6 ring system, n=0, 1, 2, 3, or 4, and selected from the group consisting of:
N,N-diethyl succinic acid amid -3,3,5-trimethylcyclohexylester (S2),
N,N-dimethyl succinic acid amid -2,3,6-trimethylcyclohexylester (S3),
3,3,5-trimethylcyclohexyl-N-ethylsuccimat (S4),
2-(isopropylcyclohexyl) 4-(dimethylamino)-4-oxo-butanoate (S5),
N,N-dimethyl-succinamic acid 3,3,5-trimethyl-cyclohexyl ester (S7),
(3,3,5)-trimethylcyclohexyl) 4-oxo-4-(1-piperidyl)butanoate (S8),
3,3,5-trimethylcyclohexyl) 3-(dimethylamino)-3-oxo-propanoate (S9),
3,3,5-trimethylcyclohexyl) 5-(dimethylamino)-5-oxo-pentanoate (S10), with a cream base.

* * * * *